US010154976B2

(12) United States Patent
Bordoloi et al.

(10) Patent No.: US 10,154,976 B2
(45) Date of Patent: *Dec. 18, 2018

(54) SYSTEM AND METHOD FOR DELIVERING PROTEASE INHIBITORS

(71) Applicant: Bordoloi Biotech, LLC, Bridgewater, NJ (US)

(72) Inventors: Binoy K Bordoloi, Bridgewater, NJ (US); Nayan J Sarma, Kamamazoo, MI (US); Rodney L. Eisenberg, Richmond, KY (US)

(73) Assignee: Bordoloi Biotech, LLC, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/432,841

(22) Filed: Feb. 14, 2017

(65) Prior Publication Data
US 2017/0165215 A1 Jun. 15, 2017

Related U.S. Application Data

(60) Division of application No. 14/964,728, filed on Dec. 10, 2015, now Pat. No. 9,603,965, which is a (Continued)

(51) Int. Cl.
*A61K 31/195* (2006.01)
*A61K 9/16* (2006.01)
(Continued)

(52) U.S. Cl.
CPC .......... *A61K 31/195* (2013.01); *A61K 9/0053* (2013.01); *A61K 9/14* (2013.01);
(Continued)

(58) Field of Classification Search
CPC ... A61K 31/195; A61K 9/0053; A61K 9/1647
See application file for complete search history.

(56) References Cited

U.S. PATENT DOCUMENTS

2004/0247686 A1* 12/2004 Okada ............... A61K 31/19
424/488
2009/0215898 A1* 8/2009 Moore ............... A61K 9/2009
514/561

OTHER PUBLICATIONS

Moritera, et al., "Microspheres of Biodegradable Polymers as a Drug-Delivery System in the Vitreous", Investigative Ophthalmology & Visual Science, vol. 32, May 1991, 1785-1790. (Year: 1991).*

* cited by examiner

*Primary Examiner* — Jianfeng Song
(74) *Attorney, Agent, or Firm* — Davé Law Group, LLC; Raj S. Davé

(57) ABSTRACT

The disclosed invention provides a system and method of artificially retarding fibrin-based blood clot degradation via the sustained release of a protease inhibitor, such as, for example, aprotinin or tranexamic acid ("TA"). The sustained release of the protease inhibitor is accomplished through incorporation within a biodegradable polymer microsphere to produce a protease inhibitor formulation. Next, the formulation along with fibrinogen and thrombin is applied to a wound site where an outer surface of the polymer microsphere degrades in a proteolytic environment to expose and release the incorporated protease inhibitor to the surrounding hydrogel or sealant or clot matrix at the wound site.

10 Claims, 27 Drawing Sheets

Related U.S. Application Data continuation of application No. 14/172,643, filed on Feb. 4, 2014, now abandoned.

(60) Provisional application No. 61/760,943, filed on Feb. 5, 2013.

(51) Int. Cl.
*A61K 9/00* (2006.01)
*A61L 31/16* (2006.01)
*A61L 24/00* (2006.01)
*A61L 24/04* (2006.01)
*A61L 26/00* (2006.01)
*A61K 9/14* (2006.01)
*A61K 9/50* (2006.01)

(52) U.S. Cl.
CPC .............. *A61K 9/1647* (2013.01); *A61K 9/50* (2013.01); *A61L 24/001* (2013.01); *A61L 24/0015* (2013.01); *A61L 24/0042* (2013.01); *A61L 24/043* (2013.01); *A61L 26/009* (2013.01); *A61L 26/0052* (2013.01); *A61L 26/0061* (2013.01); *A61L 26/0066* (2013.01); *A61L 31/16* (2013.01); *A61L 2300/418* (2013.01); *A61L 2300/434* (2013.01); *A61L 2300/604* (2013.01); *A61L 2300/622* (2013.01); *A61L 2400/04* (2013.01)

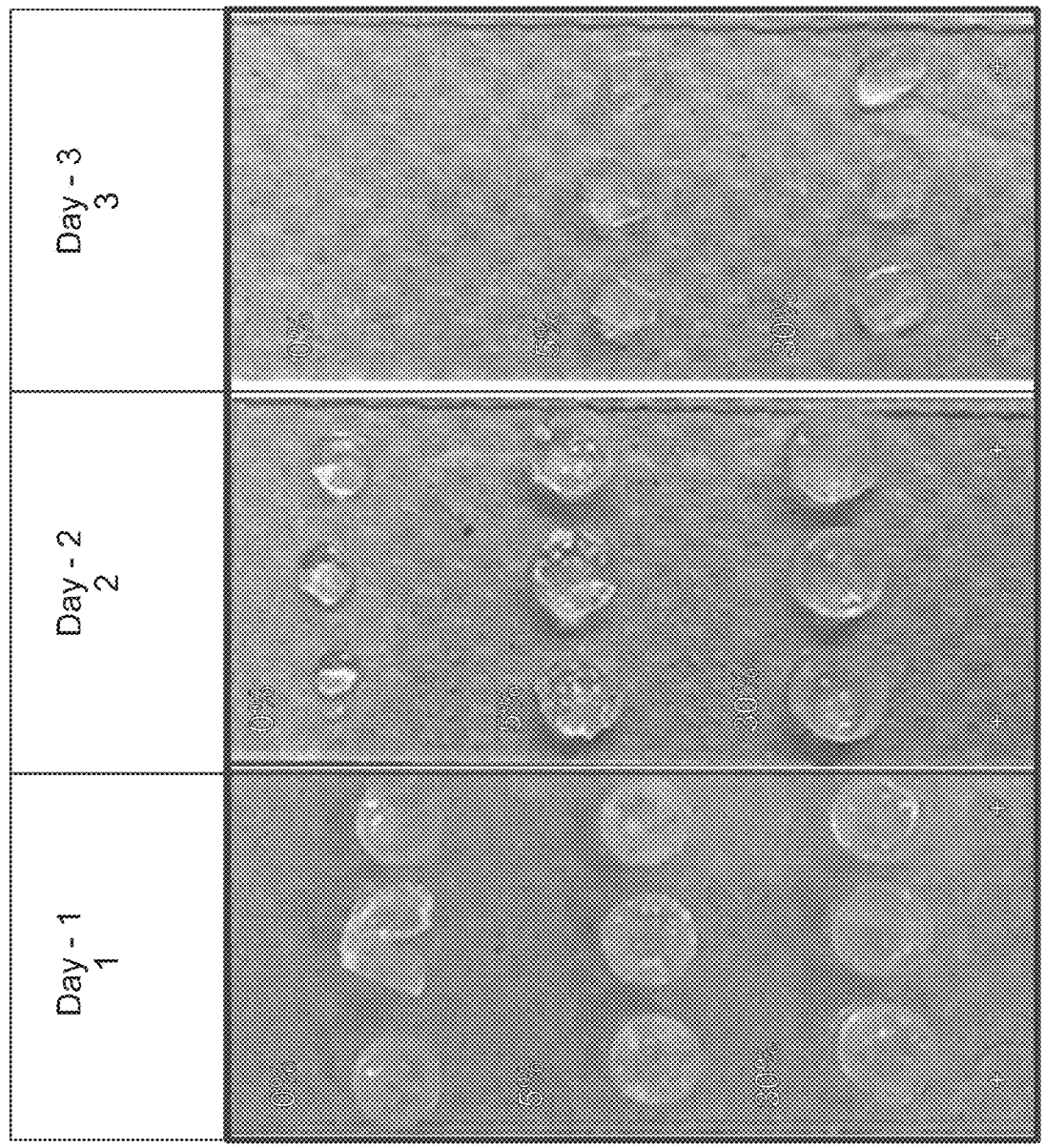

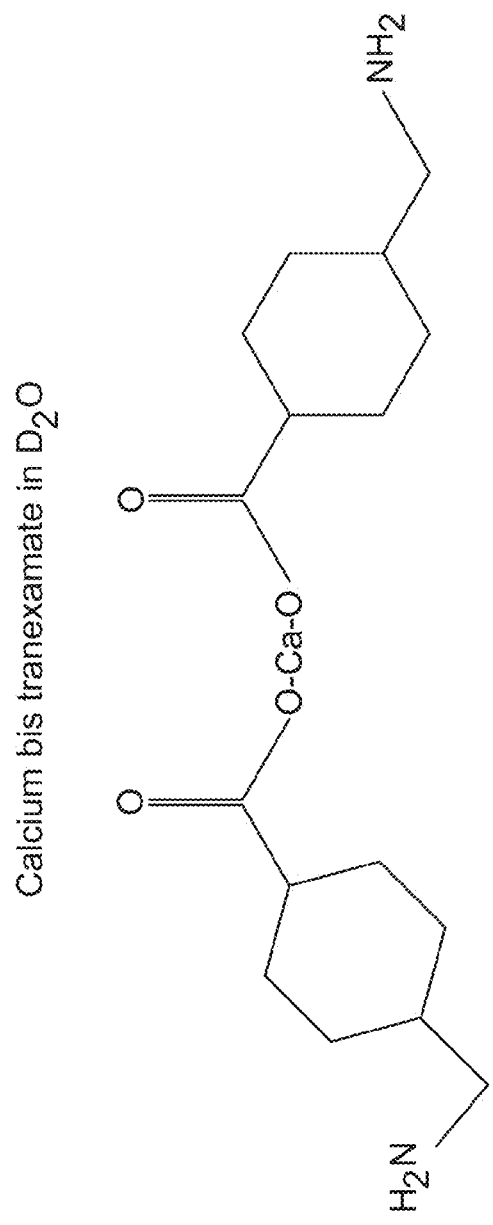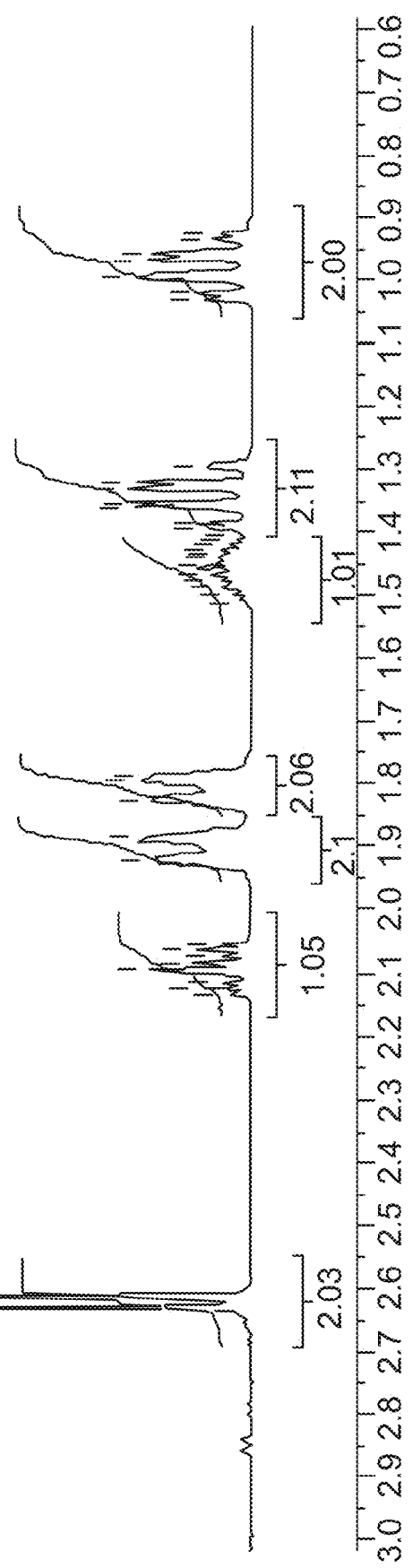
FIG. 9E

SYSTEM AND METHOD FOR DELIVERING PROTEASE INHIBITORS

PRIORITY

This disclosure claims the benefits or priority to U.S. patent application Ser. No. 14/964,728, filed Dec. 10, 2015, which claims priority to U.S. patent application Ser. No. 14/172,643, filed Feb. 4, 2014, which claims priority to U.S. Provisional Patent Application No. 61/760,973, filed on Feb. 5, 2013, the disclosures of which are incorporated herein in their entirety.

BACKGROUND

1. Technical Field

The present invention generally relates to a system and a method for delaying the dissolution of blood clots, and more particularly, the present invention provides a method and a delivery system for a material which delays the degradation of fibrin based blood clots.

2. Background of the Invention

Fibrin is insoluble protein produced by the body in response to bleeding, and is a major component in blood clots. Fibrin based clots form naturally during hemostasis, which is a process that stops bleeding by converting blood from a liquid to a solid. Fibrin is formed from fibrinogen, a soluble protein produced by the liver. Fibrinogen is converted at a wound site into fibrin by the action of thrombin, a clotting enzyme, in instances of tissue damage. Fibrin molecules may combine to form fibrin threads that mesh with platelets to form an initially soft mass. The soft mass may later harden and contract to form a rigid blood clot.

A fibrin gel may be used as a natural scaffold in tissue engineering. In one instance, a cross-linked fibrin sealant may be synthesized in vitro by combining aqueous solutions of fibrinogen and thrombin in the presence of a calcium ion (e.g., calcium chloride). This produces a fibrin sealant that resembles a physiological clot. Such fibrin sealants may be useful in surgery as an adjunct to sutures and staples. For example, severe, deep and/or artificial (i.e. as caused by a surgical incision) wounds may require that sealant mechanical strength and tissue bonding be retained until the wound fully heals. This process may take as long as fourteen days. Therapeutics is another area of use for fibrin sealants, for example in the treatment of Menorrhagia (heavy menstrual bleeding, "HMB", whereby such sealants may be administered orally or intravenously).

Fibrin sealants degrade in the presence of proteases and other enzymes in the body. For example, fibrin sealants degrade in two to three days in vivo from proteases, such as plasmin, in a wet environment. Plasmin is a serine protease. The body then absorbs the remnants of the fibrin sealant.

Rapid degradation of clots is not always welcome, particularly when deep wounds take longer to heal. Degradation of tissue engineered fibrin constructs may be delayed in vitro by fibrinolytic inhibitors, such as, aprotinin. Aprotinin, a protease inhibitor, slows or stops fibrinolysis by inhibiting plasmin. However, currently available treatments using Aprotinin often struggle to provide a safe and reliable therapeutic method to delay the degradation of fibrin clots, or fibrinolysis.

An alternative fibrinolysis inhibitor is trans-4-aminomethyl-cyclohexane-1-carboxylic acid, commonly referred to as tranexamic acid (TA). TA, often recommended for cardiac surgery, reversibly blocks lysine-binding sites on plasminogen, a plasmin proenzyme present in blood. By blocking lysine-binding sites on plasminogen, TA delays the conversion of plasminogen to plasmin, effectively slowly fibrinolysis. Thus less plasmin is available to dissolve and/or degrade fibrin-based blood clots.

As stated above, lower plasmin levels result in a longer fibrinolysis and degradation profile for a given fibrin-based blood clot. Applications of TA as an alternative to Aprotinin in fibrin-based cardiovascular tissue engineering is further discussed in a paper by E. Cholewinski et al., Tissue Engineering: Part A, Vol. 15, No. 11, pp 3645-3646, 3650-3652, 2009.

Research demonstrates that a TA derivative bio-adhesive swelling matrix may prevent bleeding in oral and maxillofacial surgery. The TA swelling matrix demonstrates appropriate mechanical resistance. Also, the TA swelling matrix rapidly swells to form a mico-adhesive plug upon contact with blood. The plug then may then disintegrate upon TA delivery. Localized delivery of a hemostatic agent, namely TA, in chronically anti-coagulated patients is further discussed by G. Sammartino et al., J. Carniofacial Surgery, Vol. 23, No. 6, pp 648-652, November 2012.

The protease inhibitors Aprotinin and TA, are highly water soluble and, therefore, may diffuse from a sealant, such as a fibrin sealant, under in vivo conditions. The diffusion properties and behavior of protease inhibitors from a fibrin sealant is further discussed in a paper by C. Buchta et al., Biomaterials, Vol. 26, Iss. 31, pp 6233-6241, November 2005.

Currently available technology may not adequately meet the challenges presented by the undesirable diffusion of a protease inhibitor, such as TA, from a sealant. In example, various drug delivery methodologies directed toward the controlled diffusion of embedded anti-fibronolytic agent largely disclose an initial burst of the agent followed by a slow release, rather than a prolonged and uniform delivery mechanism as often necessary for lengthy wound treatment therapies.

SUMMARY

An object of the present invention is to provide for the sustained release of a protease inhibitor that overcomes many of the drawbacks of the prior art.

Another object of the present invention is to provide an in vivo method and system for releasing the protease inhibitor. A feature of the invention is that the protease inhibitor is released over time in a proteolytic environment. Further, another feature of the system is the use of a biocompatible vehicle for time delayed delivery of protease inhibitor from absorbable PLGA microspheres. An advantage of the invented method for delivering the protease inhibitor is that the degradation of fibrin-based blood clots may be artificially prolonged as needed to treat wounds.

Yet another object of the present invention is to provide a system and a method of delivering protease inhibitor directly to a fibrin sealant. A feature of the invention is that the inhibitor is provided in the form of Ca-TA. An advantage of the invention is that it facilitates sustained protease inhibition, thereby inhibiting activity and providing a means for extending fibrin sealant longevity in vivo.

Still another object of the present invention is to provide a system and a method of delivering Ca- TA or calcium tranexamate to a wound site in vivo. A feature of the invention is that the calcium-containing compound is incorporated in an absorbable PLGA polymer microsphere. An advantage of the invention is that it imparts longevity to fibrin sealant in a proteolytic environment via a sustained release behavior in comparison to a control.

Additional features and advantages of the present invention are described in, and will be apparent from, the detailed description of the presently preferred embodiments and from the drawings.

In brief, the invention provides a system for delaying fibrinolytic degradation of a hydrogel or sealant at a surgical wound site, where the system delivers a biodegradable microsphere encapsulating a hydrophilic medicament, such as a protease inhibitor, in the presence of fibrinogen and thrombin; and an injectable biodegradable microsphere which provides a sustained release mechanism of said protease inhibitor in a proteolytic environment.

Further, the invention provides an in vivo method for delaying fibrin-based blood clot degradation, the method comprising the steps of substantially encapsulating a protease inhibitor within a biodegradable microsphere, where the microsphere has an average diameter of 26 +/−20 micron and an overall range of 5 to 102 micron, to produce a protease inhibitor formulation made by first combining the microsphere with fibrinogen and thrombin to form a mixture. Next, the mixture contacts a surgical wound site, wherein the site is defined by a proteolytic environment, for a time sufficient to degrade the microsphere and cause the inhibitor to release the encapsulated protease inhibitor from the microsphere.

The invention also provides a process for producing a calcium tranexamate, a salt of tranexamic acid, a protease inhibitor, comprising the step of mixing a methanolic solution of calcium nitrate and a solution of potassium tranexamate.

BRIEF DESCRIPTION OF THE FIGURES

FIG. 8 illustrates an image showing the degradation of fibrin clot over 3 days as caused by a Plasmin medium and without TA/PLGA microspheres.

FIG. 9E illustrates an NMR spectrum showing the splitting patterns of the various protons in Ca-TA.

DETAILED DESCRIPTION

Figure 1A:
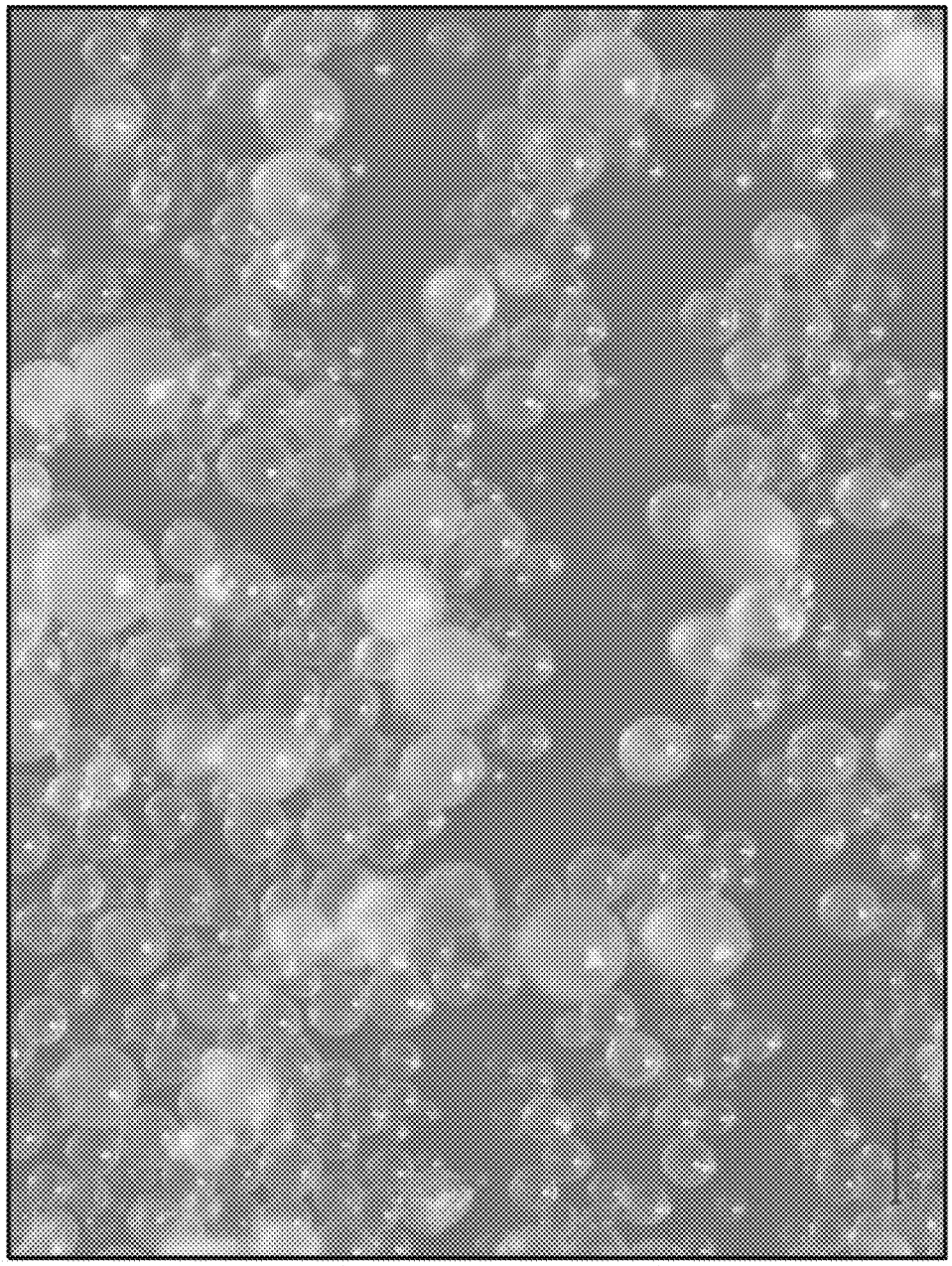
FIG. 1A illustrates an optical micrograph of 30 percent loaded TA in TA/PLGA microspheres, in accordance with features of the present invention.

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The present invention provides a solution to the unmet need for a sustained release mechanism of a protease inhibitor, such as aprotinin and/or TA, in a proteolytic environment. The sustained release mechanism may utilize a micro-encapsulated pharmaceutical agent. Also, the present invention displays unexpected behavior of a calcium salt of TA (hereinafter "Ca-TA"), a compound synthesized in this invention, in meeting the stated objective in an aqueous solution.

An embodiment of the present invention discloses a system and a method for using a micro-encapsulated pharmaceutical agent to deliver an anti-fibrinolytic agent, namely aprotinin and/or TA, that shows a relatively sustained and uniform aprotinin or TA delivery. The embodiment defines a system that avoids an initial burst of agent delivery currently associated with currently available micro-encapsulations. Rather, TA disperses from the surrounding microcapsule at a relatively uniform rate for a prolonged period.

Microencapsules prepared with a biodegradable encapsulating polymer, such as PLGA, provide an ideal delivery system of protease inhibitor such as, but not limited to, aprotinin, TA, its related calcium salt, Ca-TA and/or other related agents. Further, the delivery of the protease inhibitor may occur through application to the wound site as a powder along with fibrinogen and thrombin in powder form, in a non-woven or knitted surgical mesh. The powder blend may then be hydrated from water found in blood to form a clot.

Alternatively, the protease inhibitor may be delivered as a powder suspended, preferably in a thrombin solution, via a syringe along with fibrinogen solution to the wound site. As is known in the art, thrombin solution and fibrinogen solution may be sprayed onto a wound site to form a clot.

The microcapsules are water insoluble and thus will not diffuse away when placed in a hydrogel or a sealant surrounding matrix. The polymer portion of the microcapsule may biodegrade to produce its original monomers, lactic acid and glycolic acid to ultimately release an agent contained within the microcapsule to the surrounding matrix. The release of the agent may provide the hydrogel additional stability to guard against incoming proteases in an aqueous environment. Further, the system and method set forth by the present invention may impart enzymatic stability to the hydrogel or the sealant for a prolonged duration, ranging from several hours to several months.

Further, the calcium salt, Ca-TA, of a particular protease inhibitor agent, TA, may display similar protease inhibition activity as TA itself, but may not possess the adverse effects that may be associated with certain TA applications. In example, TA is known to have certain degree of neurotoxicity. Moreover, calcium is a preferred cation to form the salt with TA. However, other cations are also suitable such as magnesium, strontium, barium, zinc, and ferrous ions.

Ca-TA micro-encapsulated in PLGA microsphere demonstrates a sustained release profile of Ca-TA.

In accordance with the disclosed invention, a proof of principle for the mechanism of sustained release of protease inhibitor from microspheres produced from an absorbable poly-lactic-glycolic acid ("PLGA") polymer has been provided. PLGA microspheres of average dimension (e.g. forty micron in diameter) have been loaded with TA particles of average dimension of three microns, at a loading of five percent and thirty percent. An analytical technique using a scanning electron microscope and energy-dispersive x-ray spectroscopy ("SEM/EDX") shows TA impregnation. Confocal Raman spectroscopy shows that TA is distributed desirably more towards the center of the microsphere.

Figure 1B:
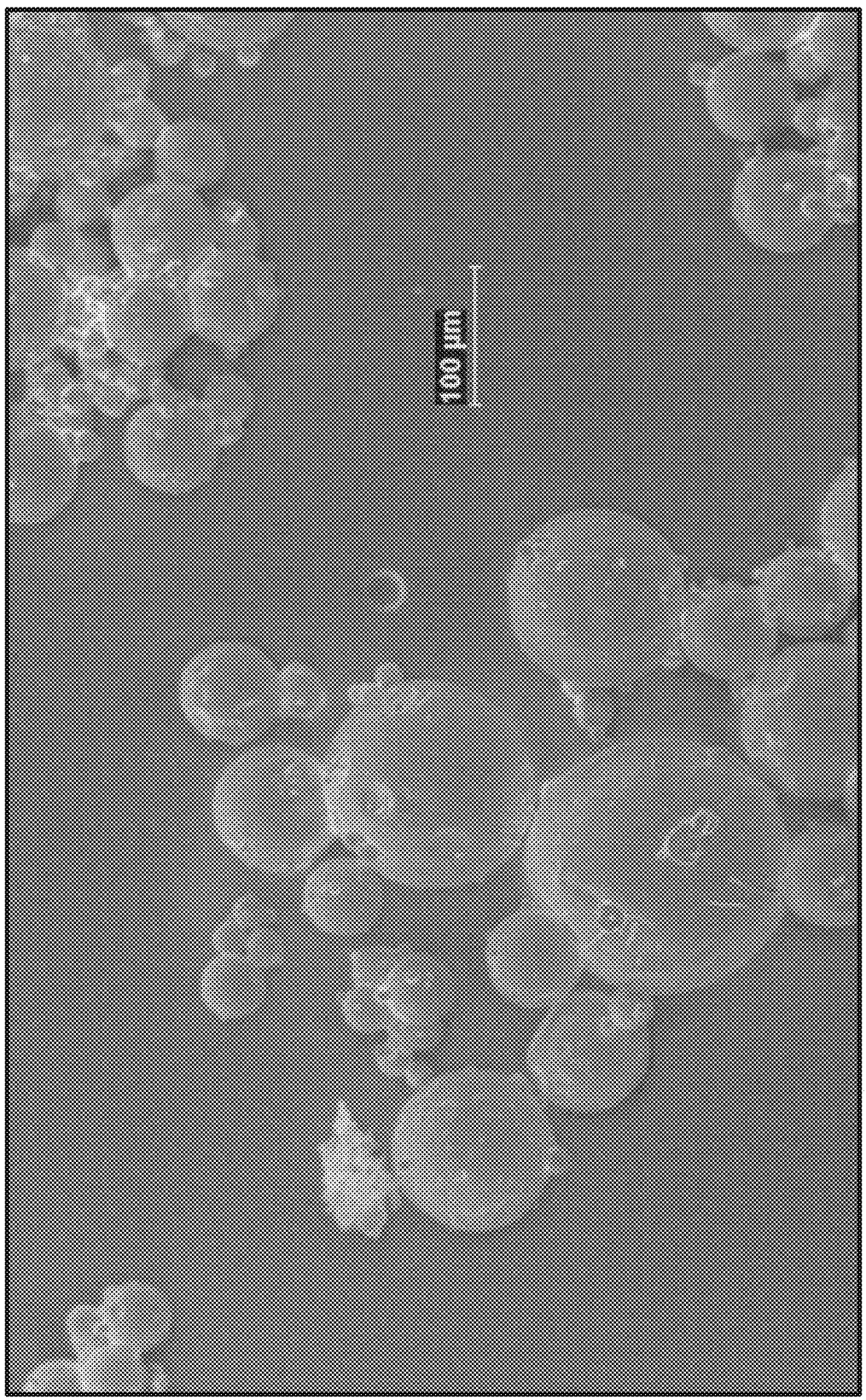
FIG. 1B illustrates an SEM micrograph of 30 percent loaded TA in TA/PLGA microspheres, in accordance with features of the present invention.

FIG. 1A illustrates an optical micrograph of 30 percent loaded TA in TA/PLGA microspheres using TA particles having an average diameter of three micron to prepare the TA/PLGA microspheres. The average dimension of each TA/PLGA microsphere is approximately forty micron in a distribution of varying sizes. Next, FIG. 1B illustrates an image of a SEM micrograph of 30 percent loaded TA in TA/PLGA microspheres; the average dimension of TA/PLGA microsphere is approximately 40 micron.

Figure 2A:
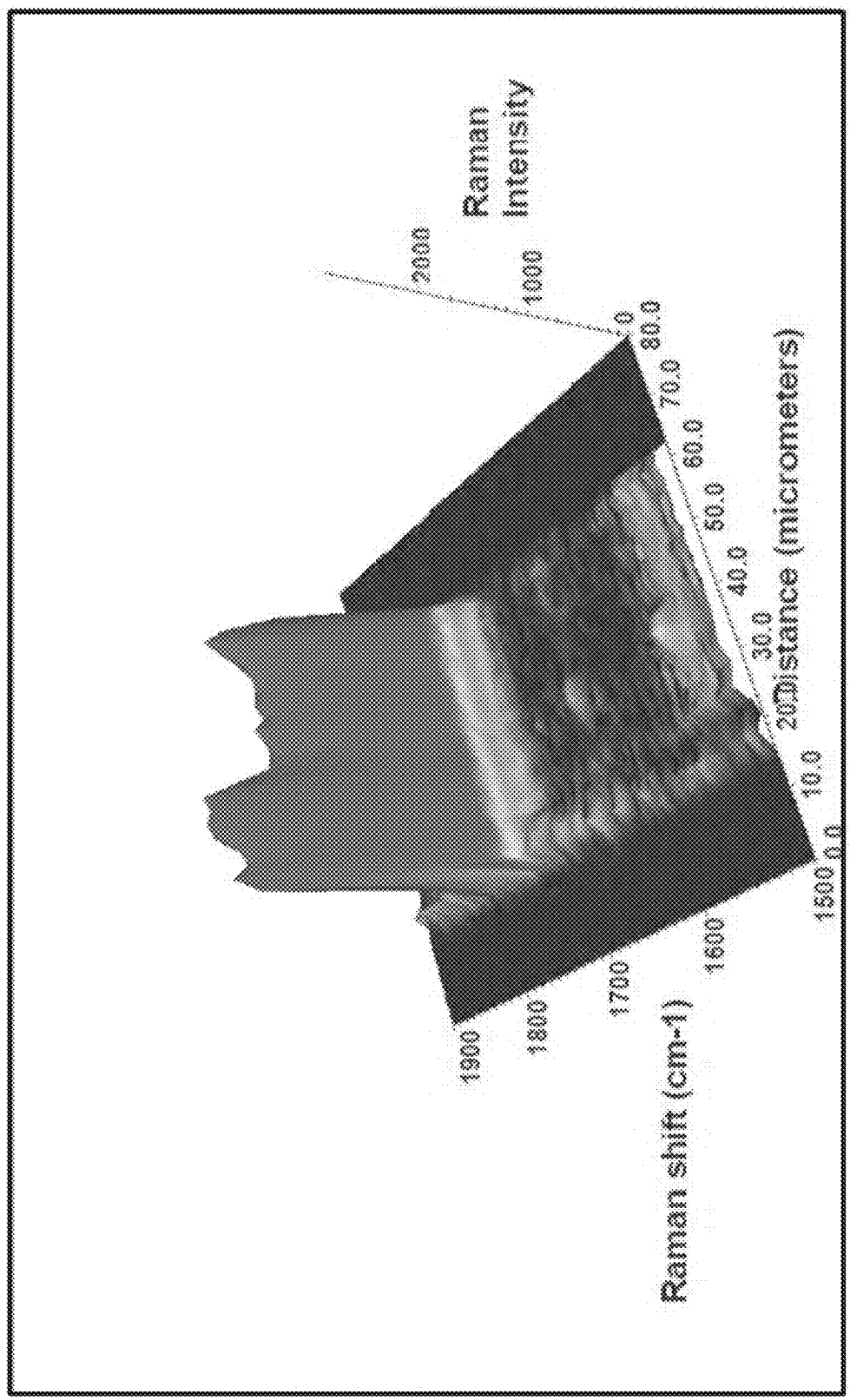
FIG. 2A illustrates an image of a Confocal-Raman spectrum showing the distribution of TA toward the center of the TA/PLGA microsphere, in accordance with features of the present invention.
Figure 2B:
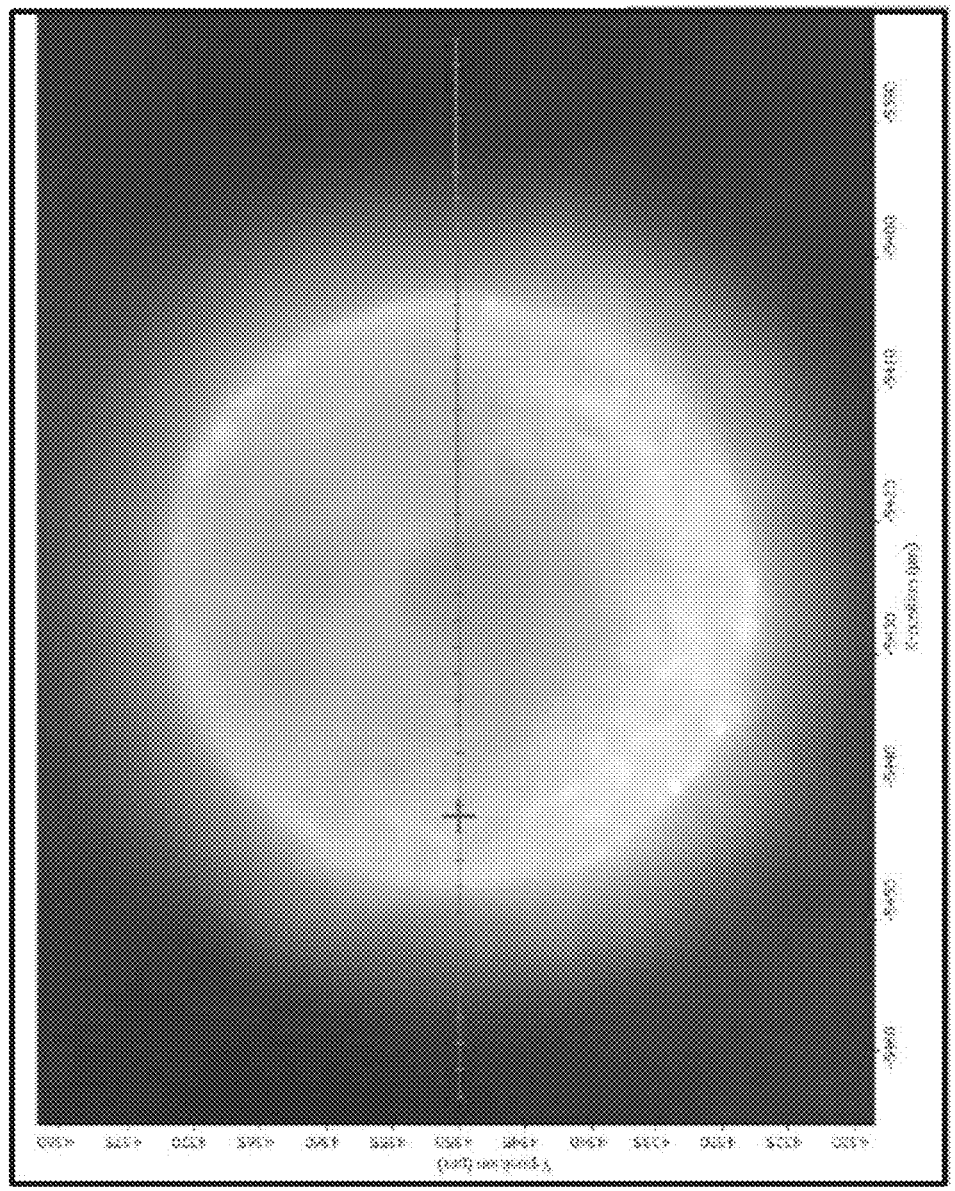
FIG. 2B illustrates an image of a TA/PLGA particle, where the Raman spectrum was collected across the width and depth.
Figure 2C:
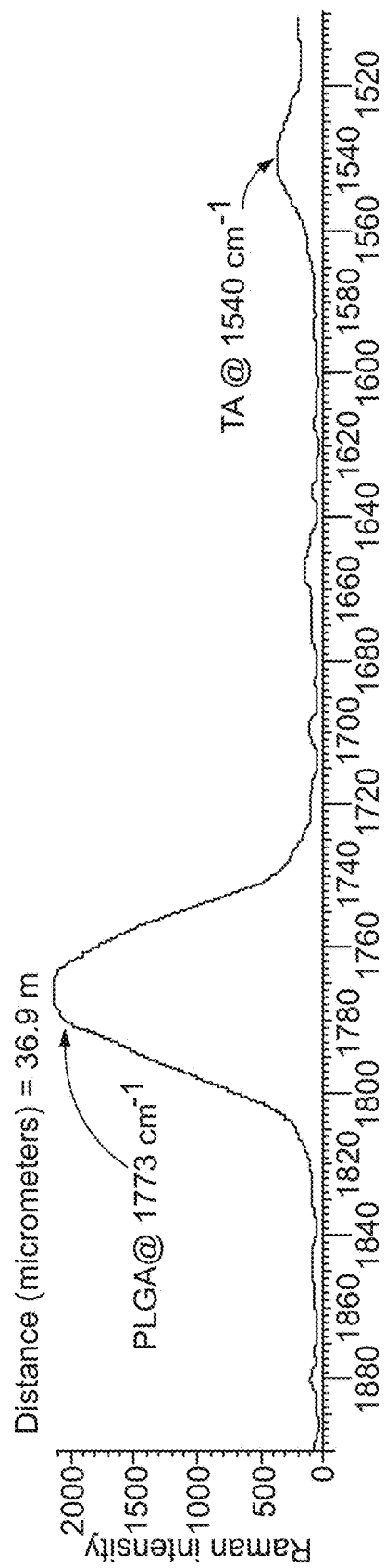
FIG. 2C illustrates a Raman spectrum of the TA/PLGA particle showing two representative bands, one band for PLGA at 1773 $cm^{-1}$ and the other band for TA at 1540 $cm^{-1}$.

FIG. 2A illustrates an image of a Confocal-Raman spectrum showing the distribution of TA toward the center of the TA/PLGA microsphere, in accordance with features of the present invention for a 30 weight percent loaded sample of TA/PLGA microsphere. Depth is shown in microns across the microsphere from 0 to 80 micron; the strongest Raman band for TA at 1540 cm-1 was found to be at the core of the TA/PLGA microsphere. FIG. 2B illustrates an image of a TA/PLGA particle, where the Raman spectrum was collected across the width and depth. FIG. 2C illustrates a Raman spectrum of the TA/PLGA particle showing two representative bands, one for PLGA at 1773 $cm^{-1}$ and the other band characteristic for TA at 1540 $cm^{-1}$.

Figure 3A:
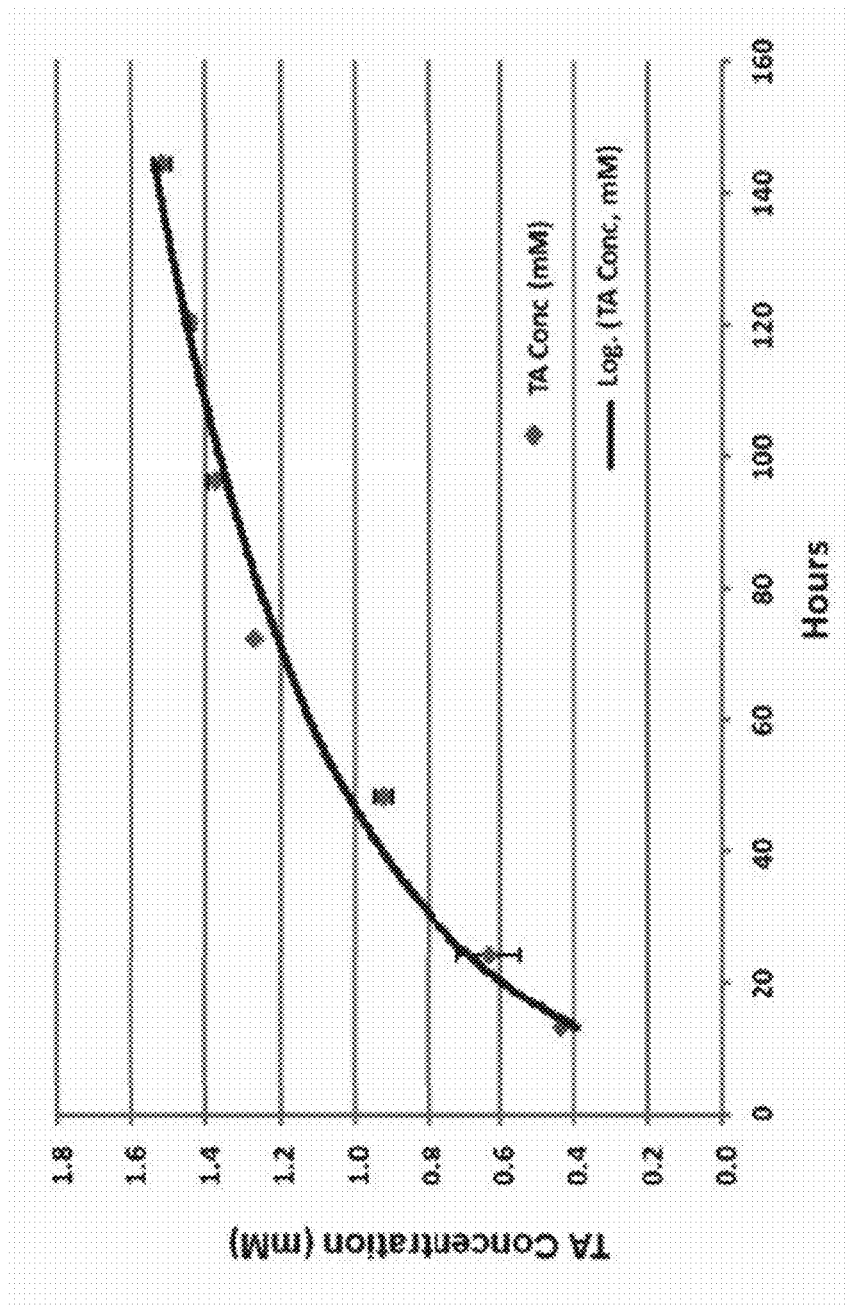
FIG. 3A illustrates a graph showing the concentration of TA, in mM units, released over time in hours from microspheres, in accordance with features of the present invention.
Figure 3B:
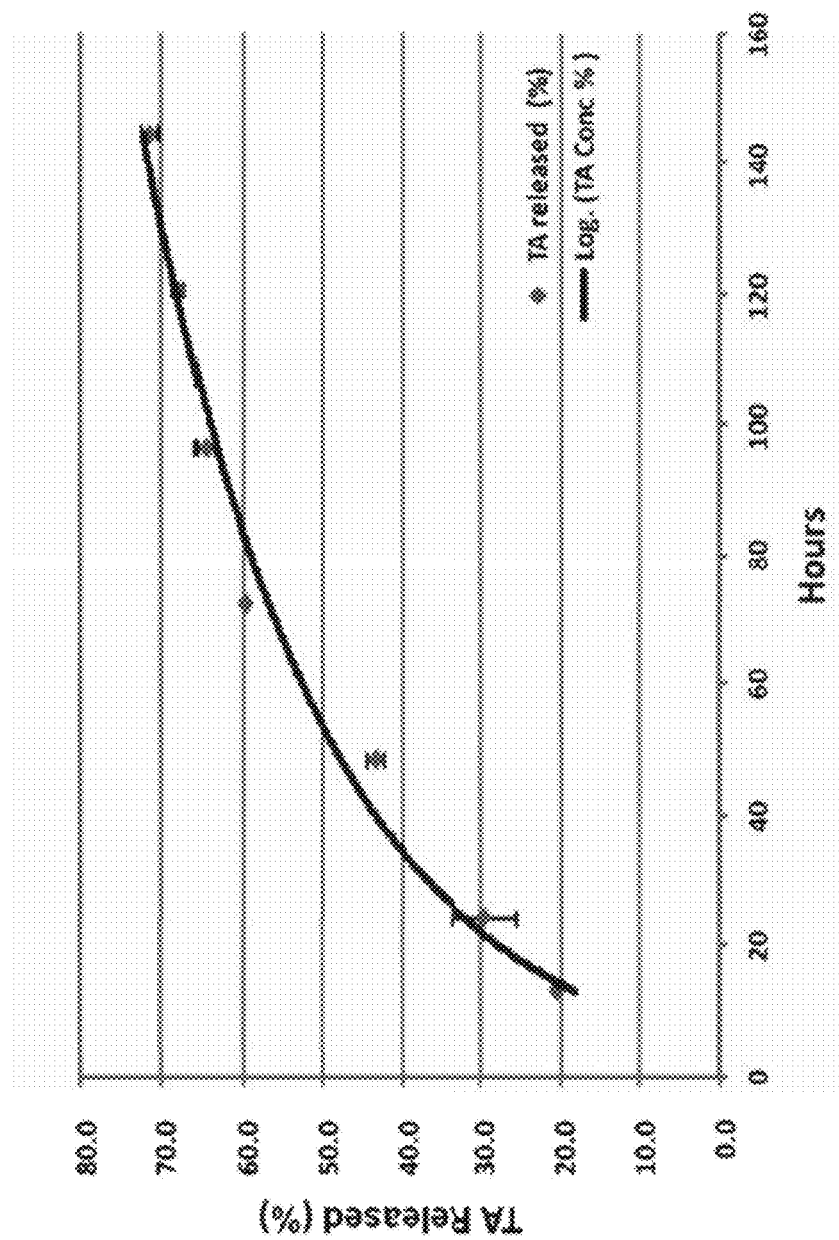
FIG. 3B illustrates the same data as of FIG. 3A as weight percent of TA released from TA/PLGA microspheres over time in hours, in accordance with features of the present invention.

FIG. 3A illustrates a graph showing the concentration of TA, in mM units, released over time in hours from microspheres, which were prepared at a strength of 20 mg TA/PLGA microspheres in 3 ml PBS buffer of pH 7.4 at 37° C.; the data was curve-fitted in a log scale. Similarly, FIG. 3B illustrates the same data of FIG. 3A, but instead shows the weight percent TA released from TA/PLGA microspheres over time in hours, where data were collected until about 70 percent of the maximum releasable TA was achieved.

Figure 4:
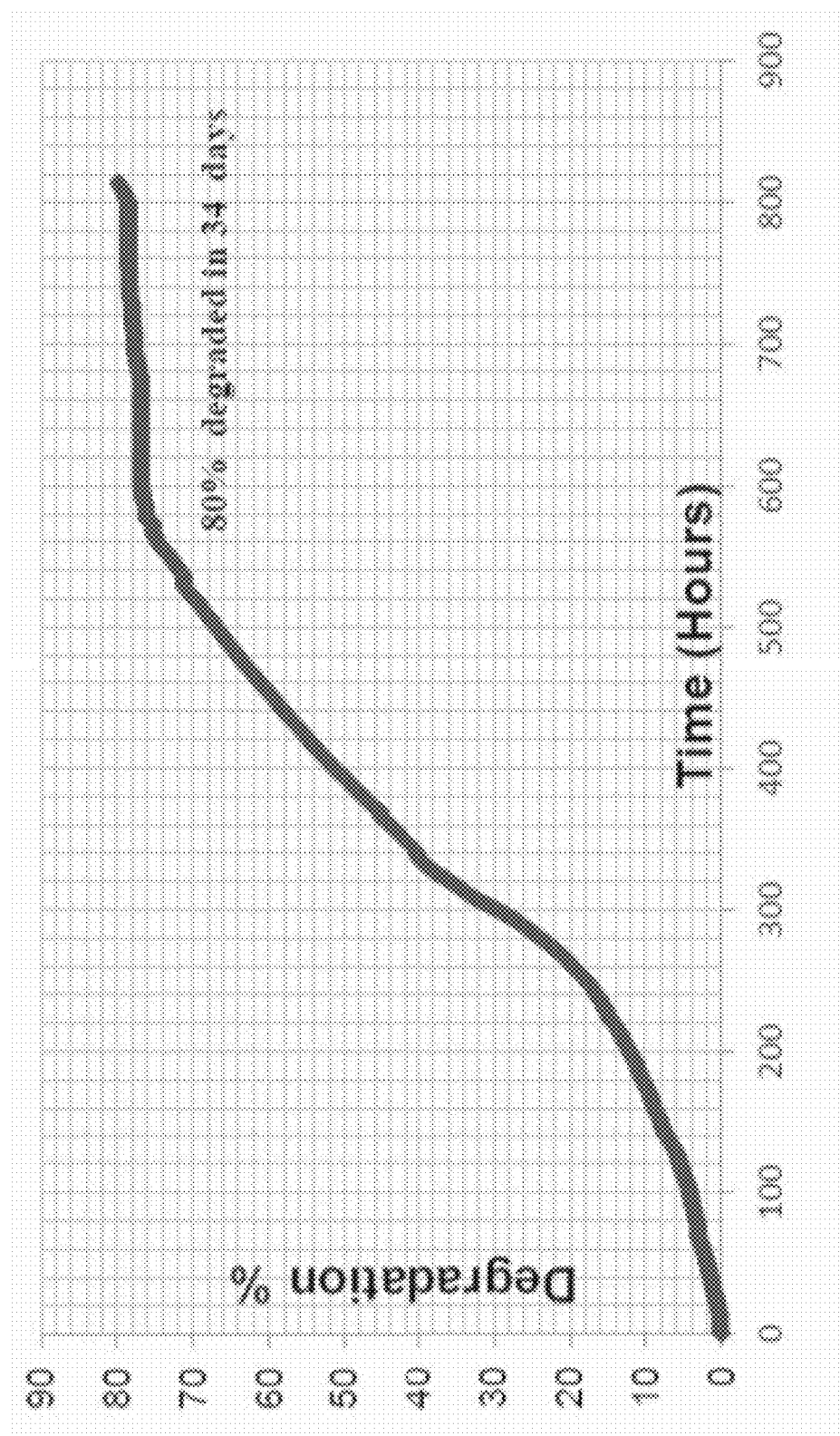
FIG. 4 illustrates a graph showing the hydrolytic degradation profile of a placebo PLGA microsphere in de-ionized water at 37° C.

FIG. 4 illustrates a graph showing the hydrolytic degradation profile of a placebo PLGA microsphere in de-ionized water at 37° C.

Figure 5:
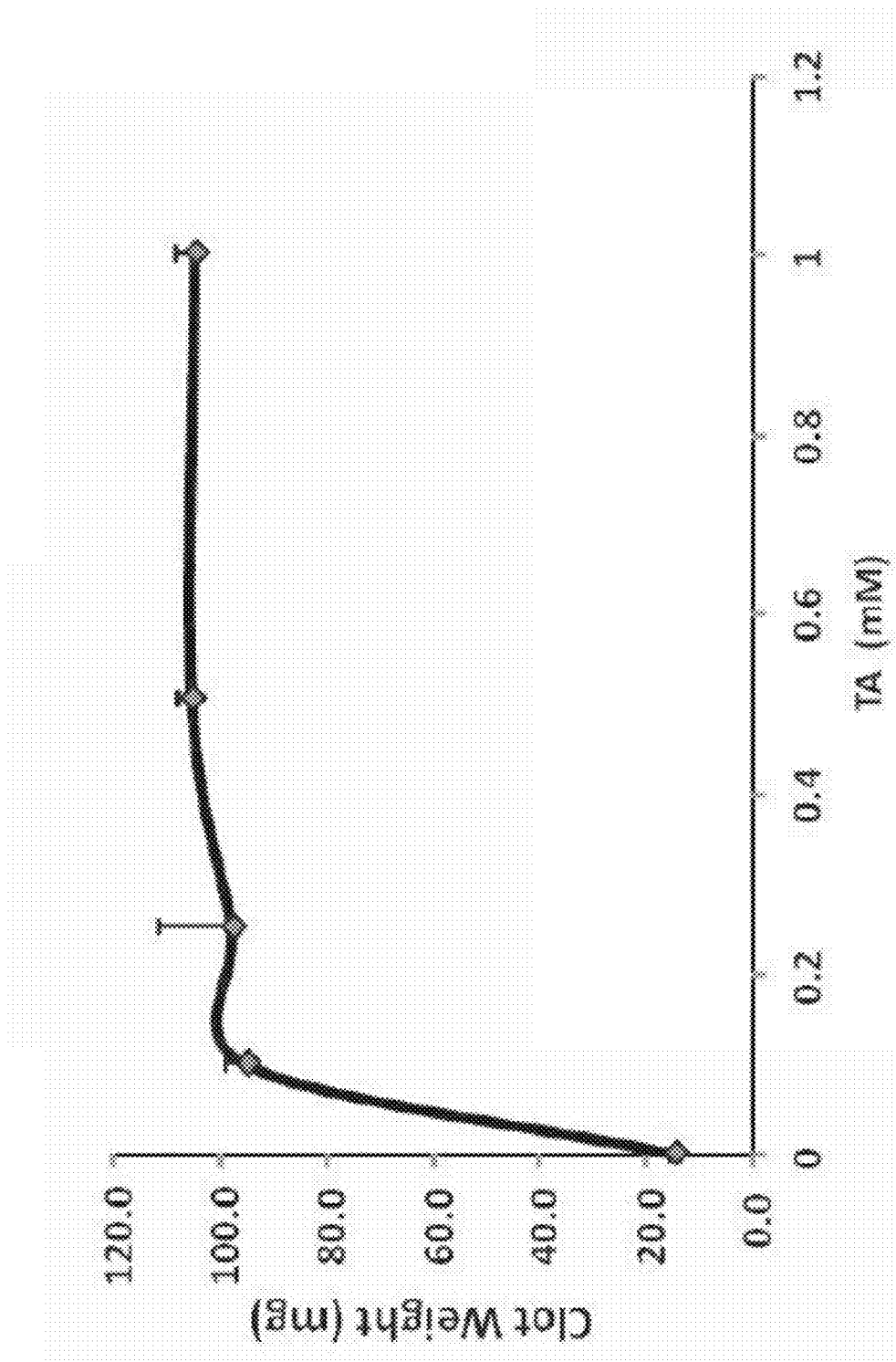
FIG. 5 illustrates a graph showing fibrin clot weight measured against TA concentration.

FIG. 5 illustrates a graph showing fibrin clot weight measured against TA concentration, demonstrating the minimum concentration of TA required for achieving 100 percent clot stability.

Figure 6:
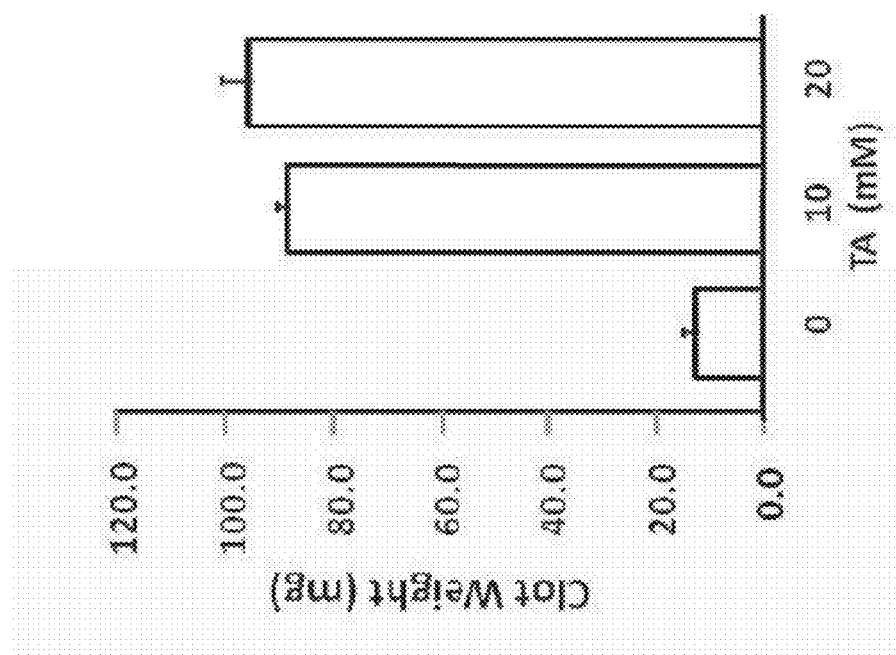
FIG. 6 illustrates a graph showing fibrin clot weight measured against total TA concentration in microspheres, in accordance with features of the present invention.

FIG. 6 illustrates a graph showing fibrin clot weight measured against total TA concentration in microspheres, where TA/PLGA microspheres were used, demonstrating the minimum concentration needed for achieving 100 percent clot stability.

Figure 7:
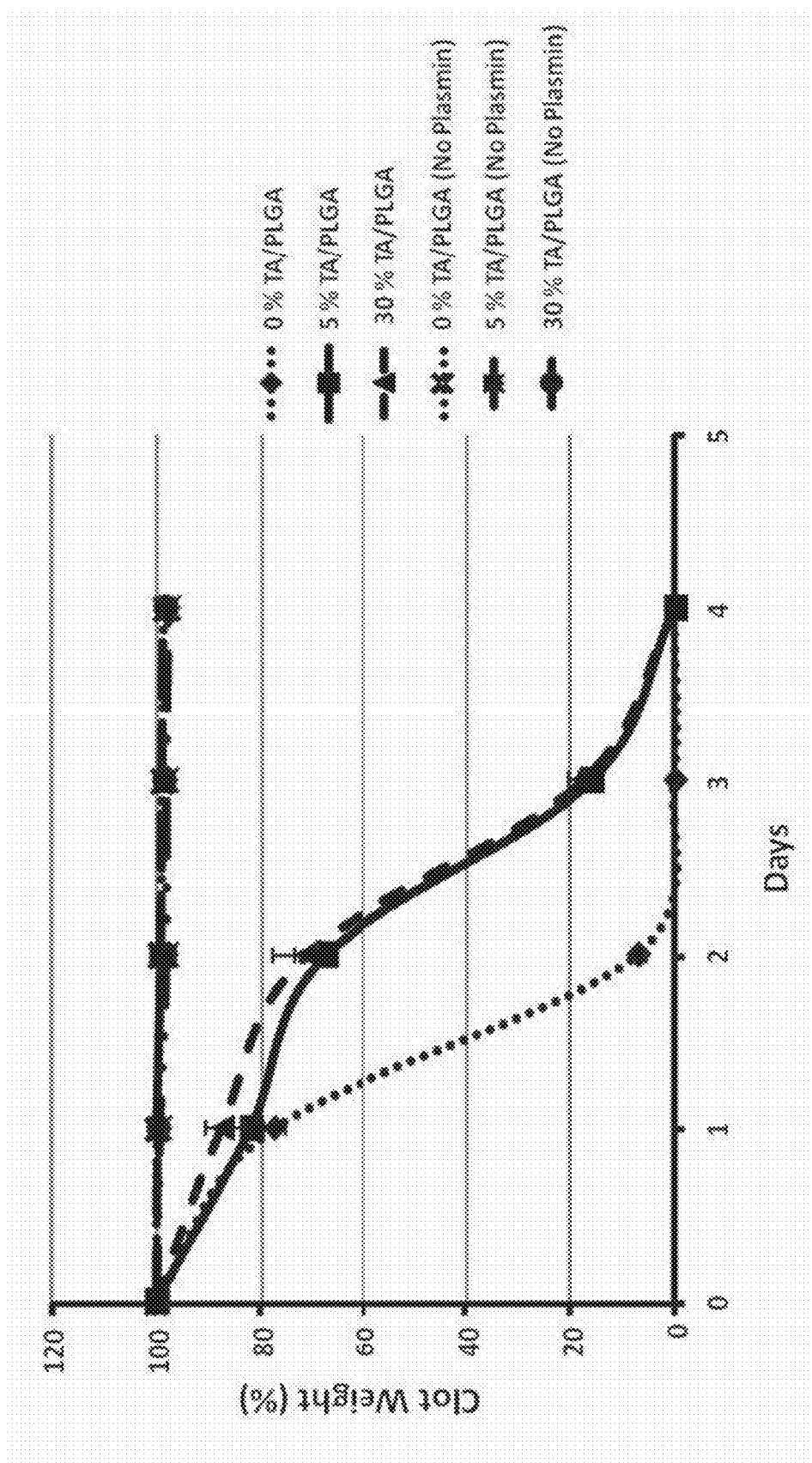
FIG. 7 illustrates a graph showing fibrin clot weight percent in a plasmin medium as a function of time in days for 5 percent and 30 percent loaded TA/PLGA microsphere containing clots (total TA concentration held constant at 3.5 mM), in accordance with features of the present invention.

FIG. 7 illustrates a graph showing fibrin clot weight percent in a plasmin medium as a function of time in days for 5 weight percent and 30 weight percent loaded TA/PLGA microsphere containing clots (total TA concentration held constant at 3.5 mM) as compared to a control containing 0 percent TA/PLGA (that is no TA/PLGA). Also shown are results when there was no Plasmin.

FIG. 8 illustrates an image showing the degradation of fibrin clot over 3 days as caused by a Plasmin medium at a pH of 7.4 at 37° C. with (both 5 percent and 30 percent loaded microspheres) and without TA/PLGA microspheres.

Figure 9A:
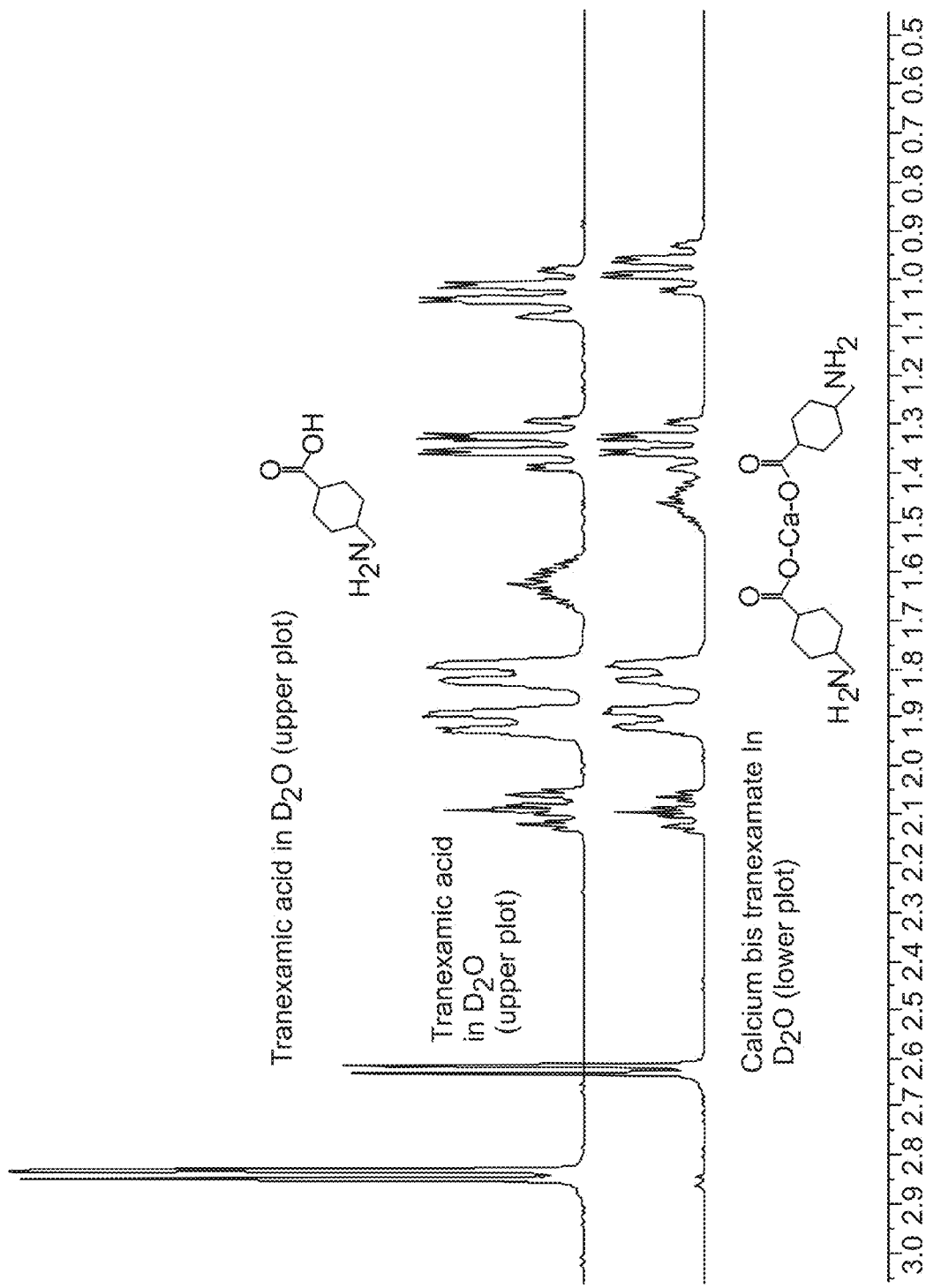
FIG. 9A illustrates an image showing NMR spectra comparison of TA and Ca-TA (Calcium Tranexamate or bis-Tranexamate) in $D_2O$ solvent.
Figure 9B:
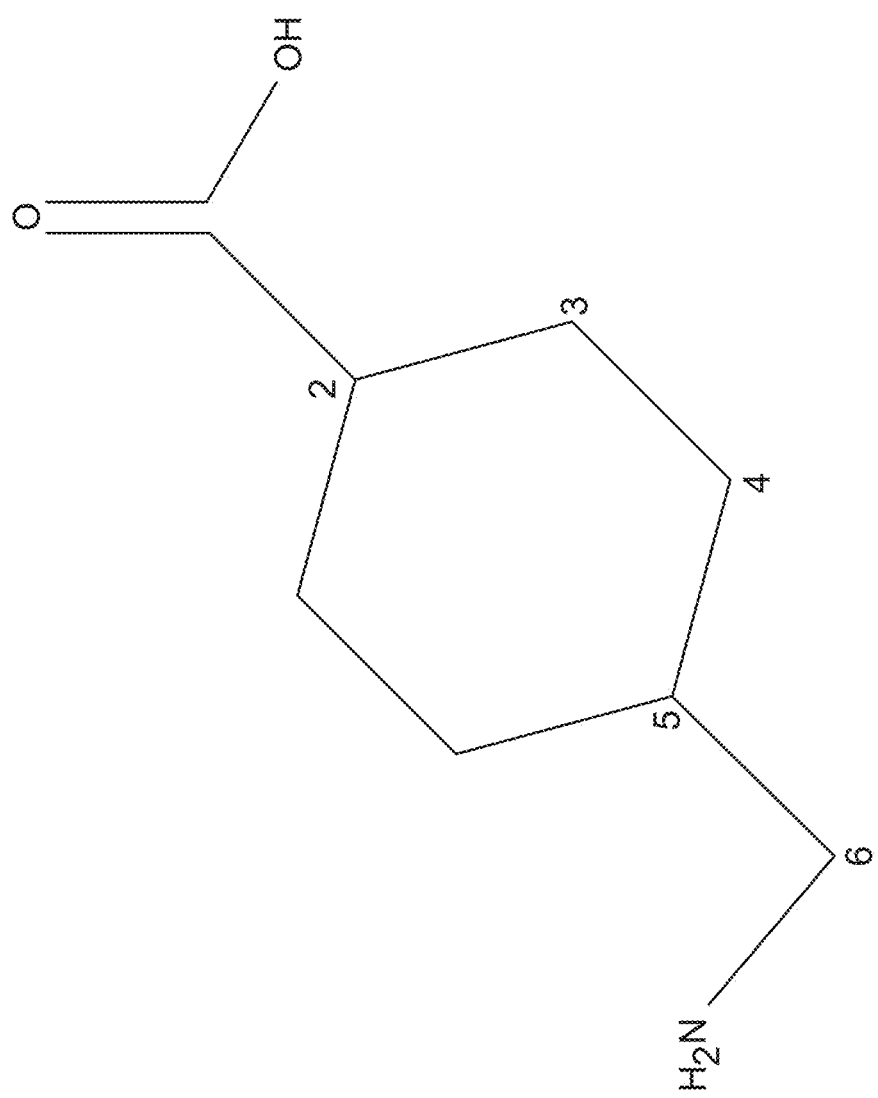
FIG. 9B illustrates a chemical structure for TA including a numerical identification of Carbon atoms for their associated NMR characterization.
Figure 9C:
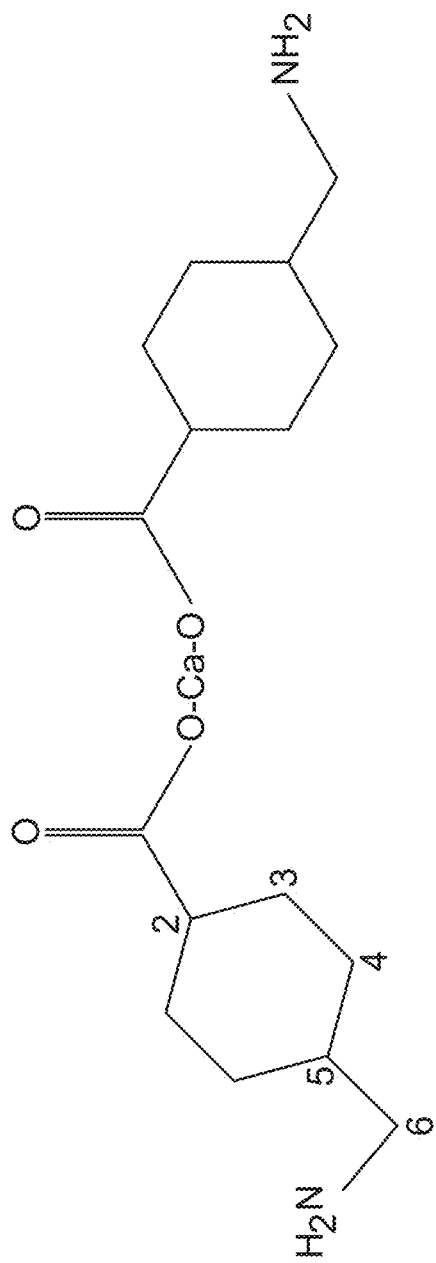
FIG. 9C illustrates a chemical structure for Ca-TA including a numerical identification of Carbon atoms for their associated NMR characterization.
Figure 9D:
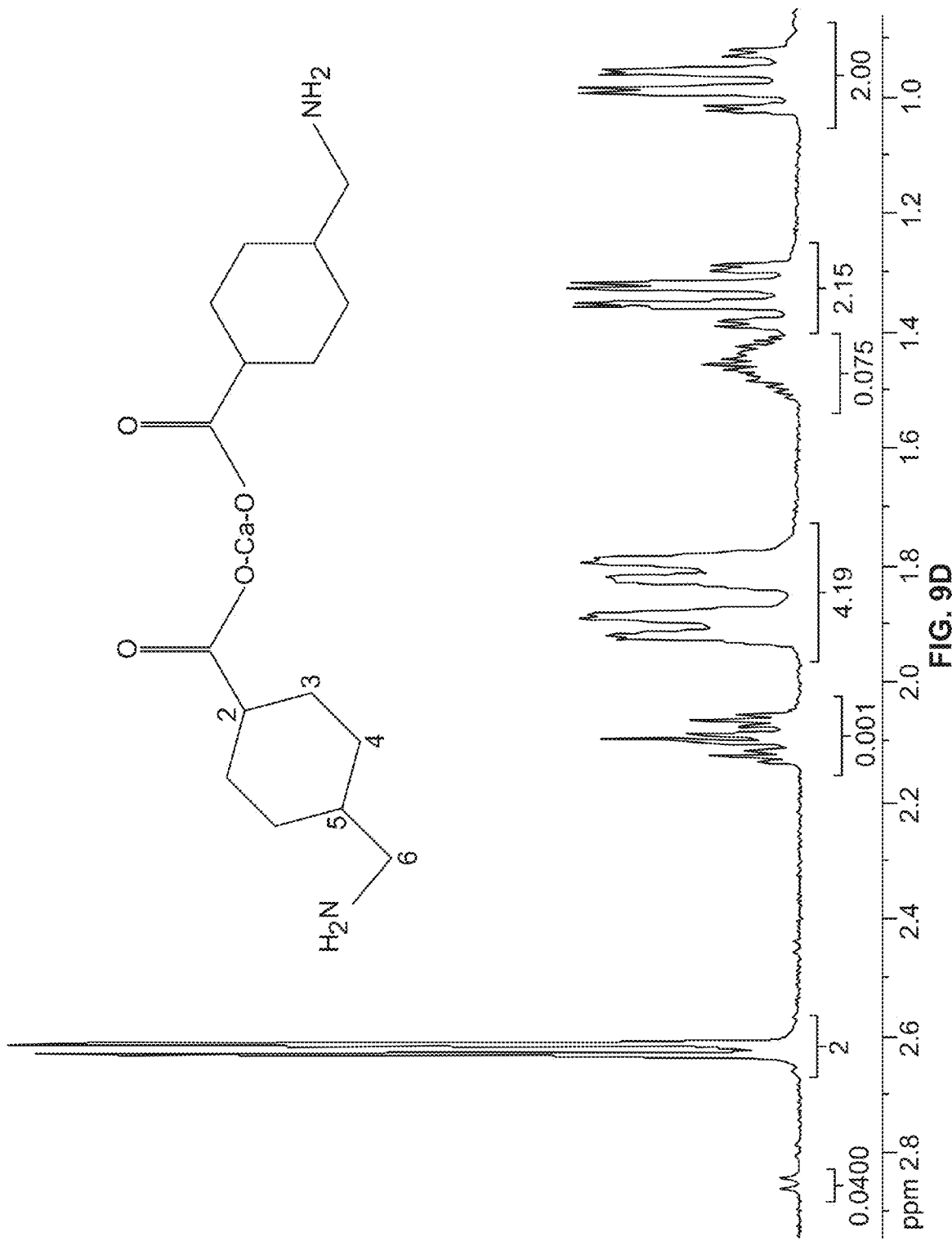
FIG. 9D illustrates an NMR spectrum identifying the protons at various chemical shifts in ppm for the carbon positions as shown in the skeletal formula for Ca-TA.

FIG. 9A illustrates an image showing NMR spectra comparison of TA and Ca-TA (Calcium Tranexamate or bis-Tranexamate) in $D_2O$ solvent. FIG. 9B illustrates a chemical structure for TA including a numerical identification of Carbon atoms for their associated NMR characterization. FIG. 9C illustrates a skeletal formula for Ca-TA including a numerical identification of Carbon atoms for their associated NMR characterization. FIG. 9D illustrates an NMR spectrum identifying the protons at various chemical shifts in ppm for the carbon positions as shown in the skeletal formula for Ca-TA. FIG. 9E illustrates an NMR spectrum showing the splitting patterns of the various protons in Ca-TA.

Figure 10:
FIG. 10 illustrates an SEM image of 5 percent Ca-TA loaded Ca-TA/PLGA microsphere, in accordance with features of the present invention.

FIG. 10 illustrates an SEM image of 5 percent Ca-TA loaded Ca-TA/PLGA microsphere having an average diameter of 26+/−20 micron and an overall diameter range of about 5 to about 102 micron.

Figure 11:
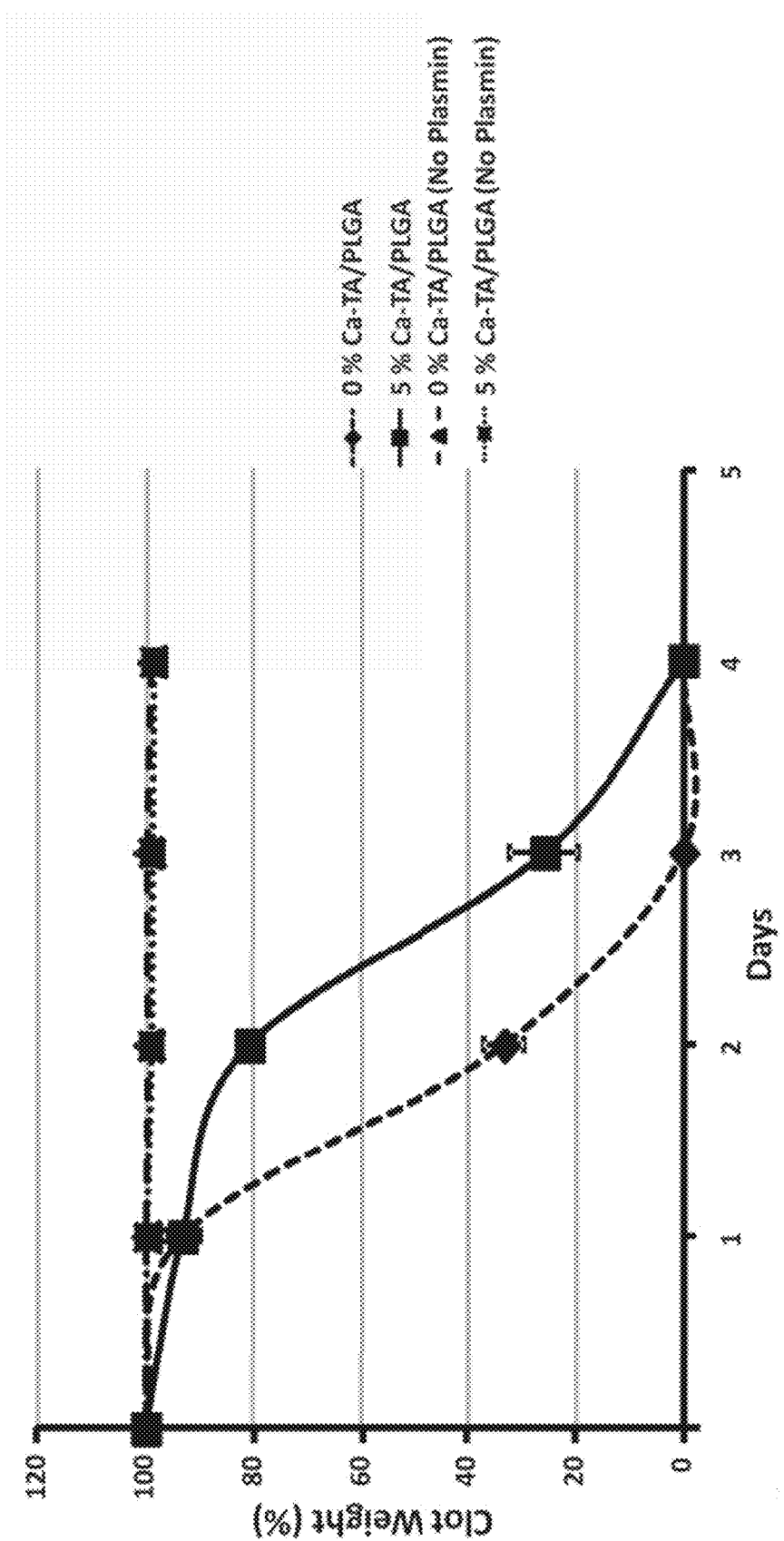
FIG. 11 illustrates a graph showing fibrin clot weight percent in a Plasmin medium as a function of time in days for clots with and without microspheres; also shown are results in a no Plasmin medium, in accordance with features of the present invention.

FIG. 11 illustrates a graph showing fibrin clot weight percent in a Plasmin medium as a function of time in days for clots with (that is 5 percent Ca-TA loaded in Ca-TA/PLGA microsphere, at a total Ca-TA concentration of 3.5 mE) and without (that is 0 percent Ca-TA/PLGA) microspheres; also shown are results in a no Plasmin medium.

Figure 12:
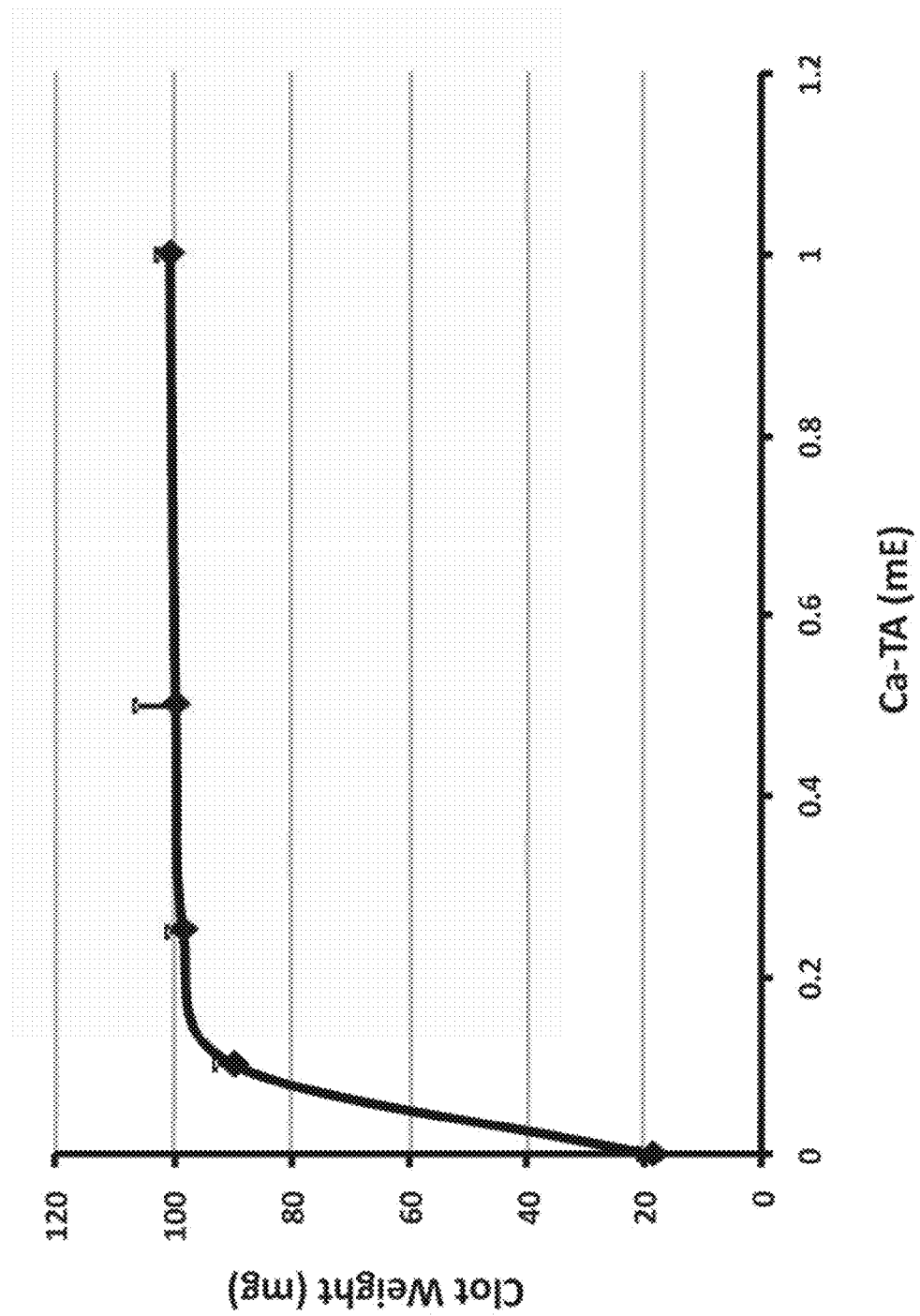
FIG. 12 illustrates a graph showing fibrin clot weight percent measured against Ca-TA concentration, in mE units.
Figure 13:
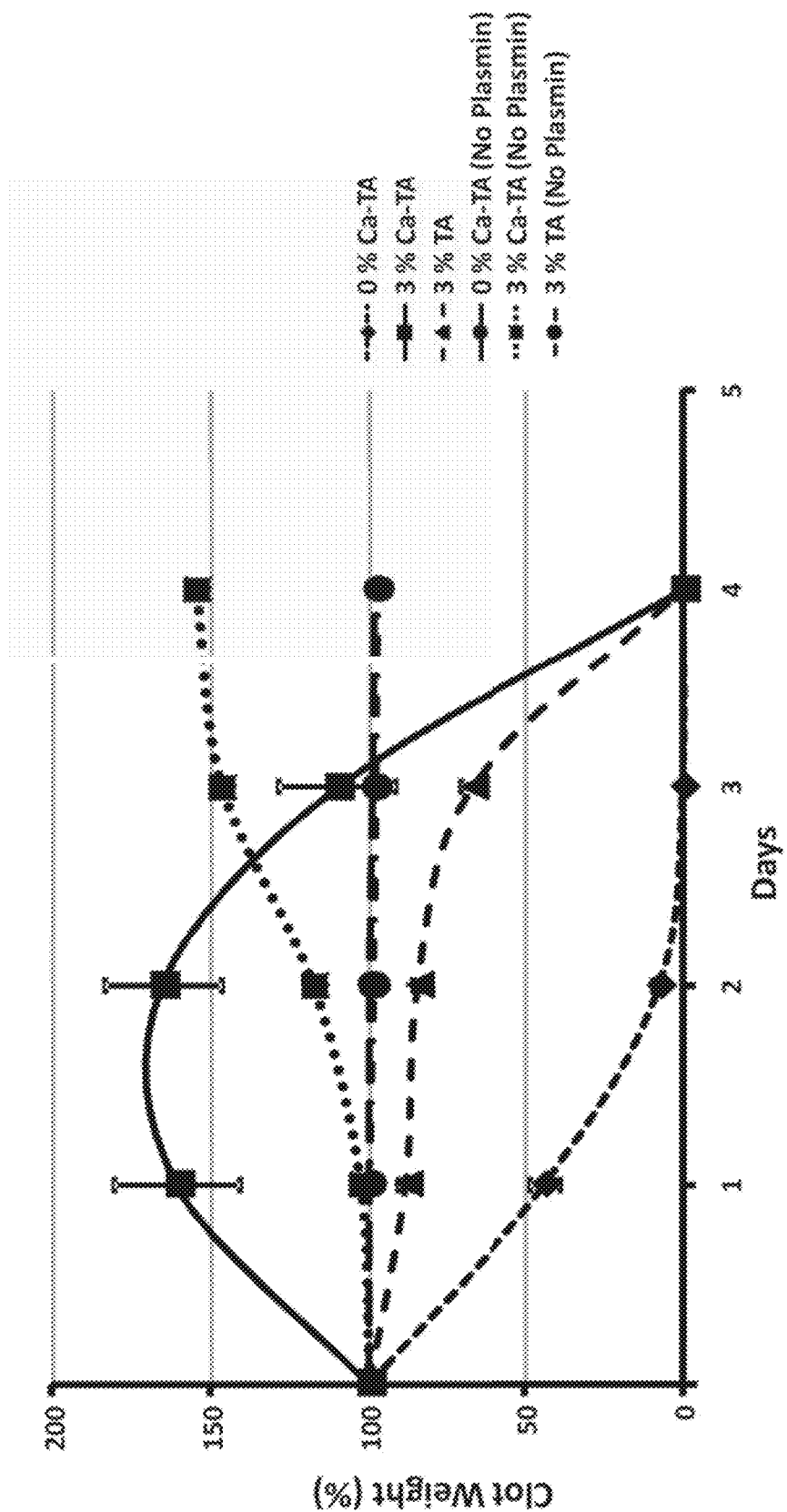
FIG. 13 illustrates a graph showing fibrin clot weight percent in a Plasmin medium as a function of time in days.

FIG. 12 illustrates a graph showing fibrin clot weight percent measured against Ca-TA concentration, in mE units, demonstrating the minimum concentration needed for achieving 100 percent clot stability FIG. 13 is a graph showing fibrin clot weight percent in a Plasmin medium as a function of time in days for 3 percent Ca-TA containing clot as compared to a control of 0 percent Ca-TA containing clot; also shown are results in a no Plasmin medium.

Figure 14:
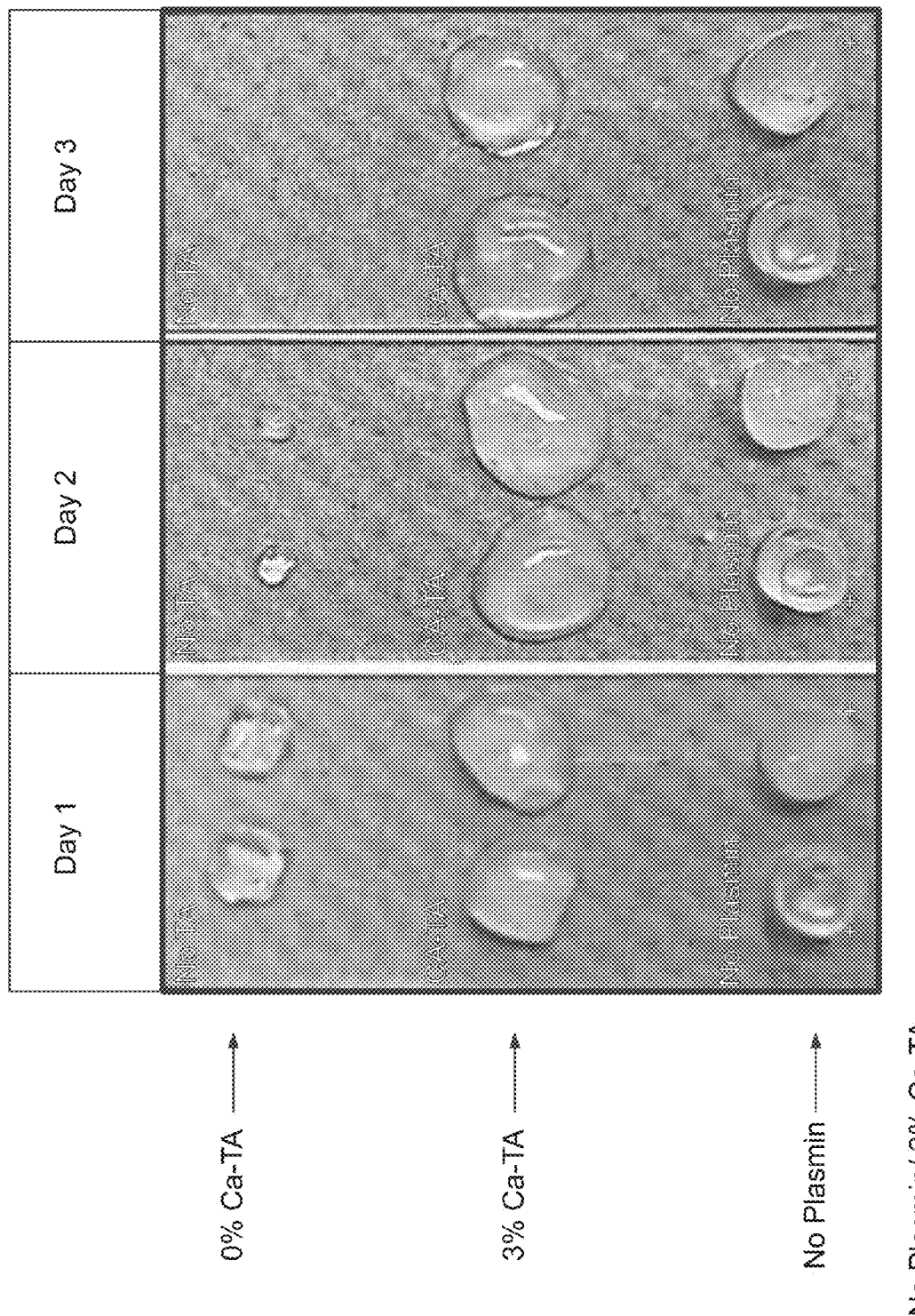
FIG. 14 illustrates an image showing the degradation of fibrin clot over 3 days as caused by a Plasmin medium with and without Ca-TA; the effect of no-plasmin medium is also shown, in accordance with features of the present invention.

FIG. 14 is an image showing the degradation of fibrin clot over 3 days as caused by a Plasmin medium at a pH of 7.4 at 37° C. with and without Ca-TA; the effect of no-plasmin medium is also shown.

Figure 15:
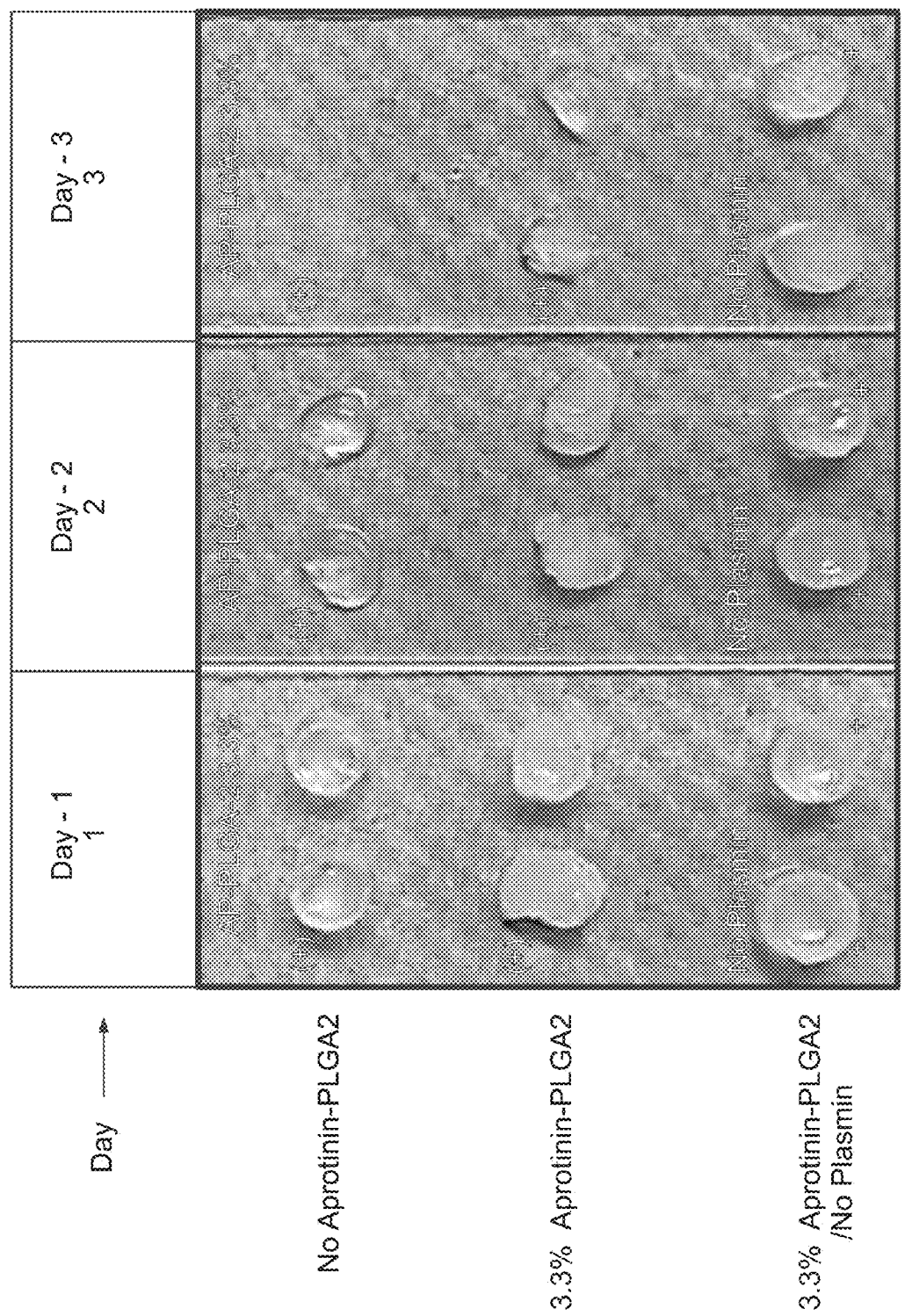
FIG. 15 illustrates an image showing the degradation of fibrin clot over 3 days as caused by a Plasmin medium with and without aprotinin.

FIG. 15 illustrates an image showing the degradation of fibrin clot over 3 days as caused by a Plasmin medium at a pH of 7.4 at 37° C. with and without aprotinin at a loading level of 3.3 percent as incorporated in PLGA microsphere; the effect of no-plasmin medium is also shown.

Figure 16:
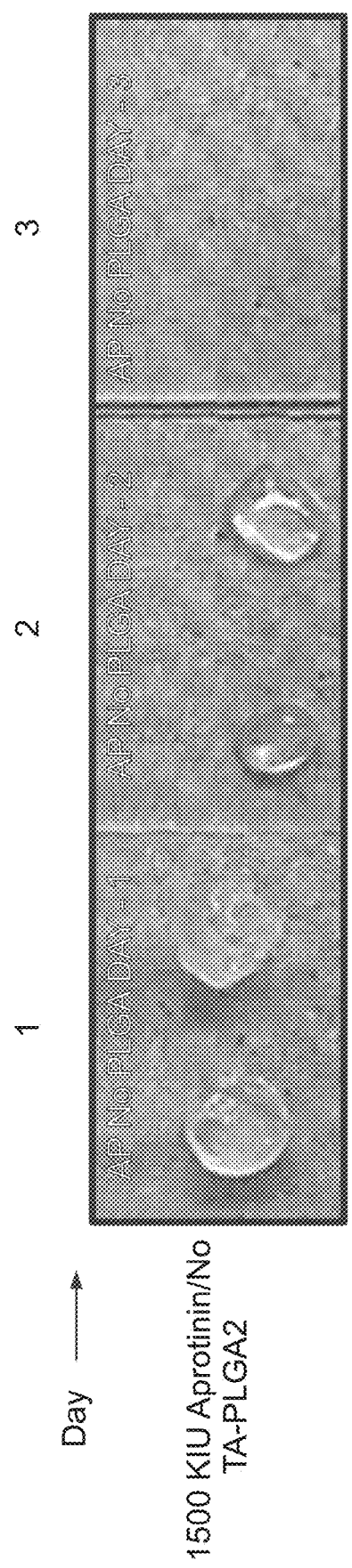
FIG. 16 is an image showing the degradation of fibrin clot treated with 1500 kallekrein inhibitor unit over time.

FIG. 16 illustrates an image showing the degradation of fibrin clot treated with 1500 KIU (kallekrein inhibitor unit, where 1 mg aprotinin=6500 KIU) over 3 days as caused by a Plasmin medium.

Figure 17:
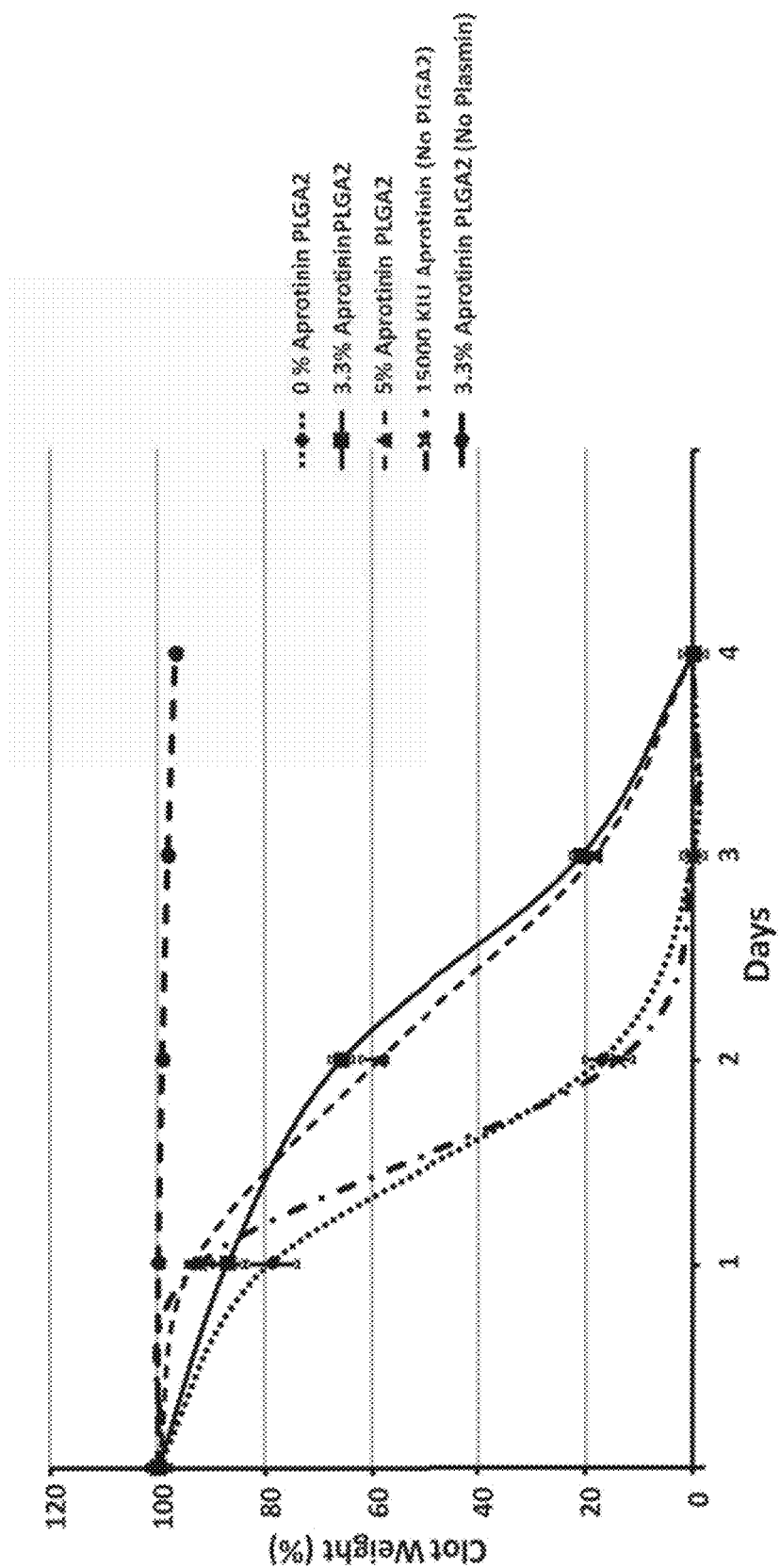
FIG. 17 illustrates a graph showing fibrin clot weight percent in a Plasmin medium as a function of time in days for loading level of 3.3 percent aprotinin in PLGA-2 containing clot.

FIG. 17 illustrates a graph showing fibrin clot weight percent in a Plasmin medium as a function of time in days for loading level of 3.3 percent aprotinin in PLGA-2 containing clot as compared to a control of loading level of 0 percent aprotinin containing clot. Also shown are results of 5.0 percent aprotinin/PLGA-2, 3.3 percent aprotinin/PLGA-2 in a no Plasmin medium, as well as aprotinin without any PLGA-2.

Figure 18:
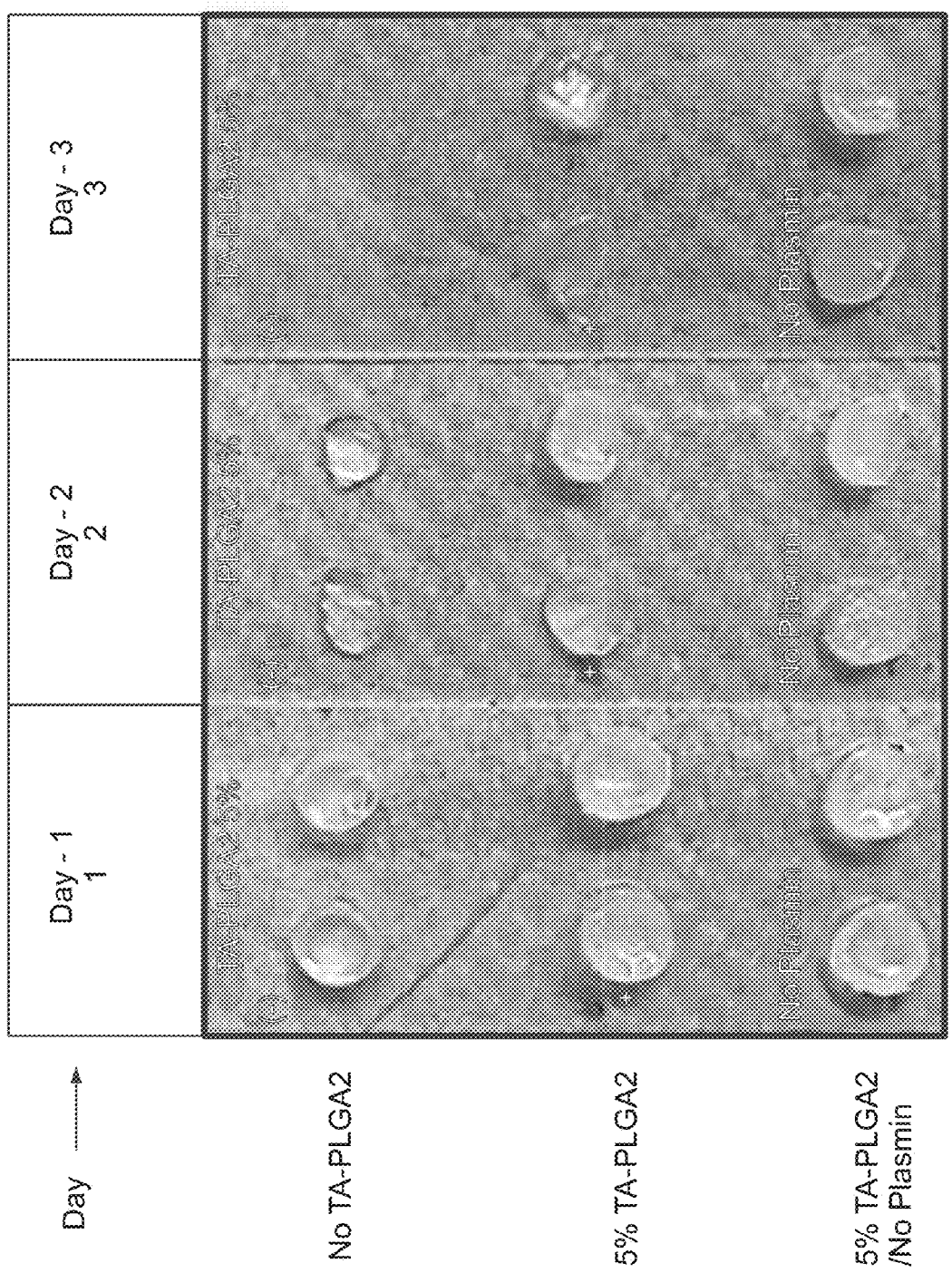
FIG. 18 illustrates an image showing the degradation of fibrin clot over 3 days as caused by a Plasmin medium with and without TA at a loading level of 5.0 percent as incorporated in PLGA-2 microsphere, in accordance with features of the present invention.

FIG. 18 illustrates an image showing the degradation of fibrin clot over 3 days as caused by a Plasmin medium at a pH of 7.4 at 37° C. with and without TA at a loading level of 5.0 percent as incorporated in PLGA-2 microsphere; the effect of no-plasmin medium is also shown.

Figure 19:
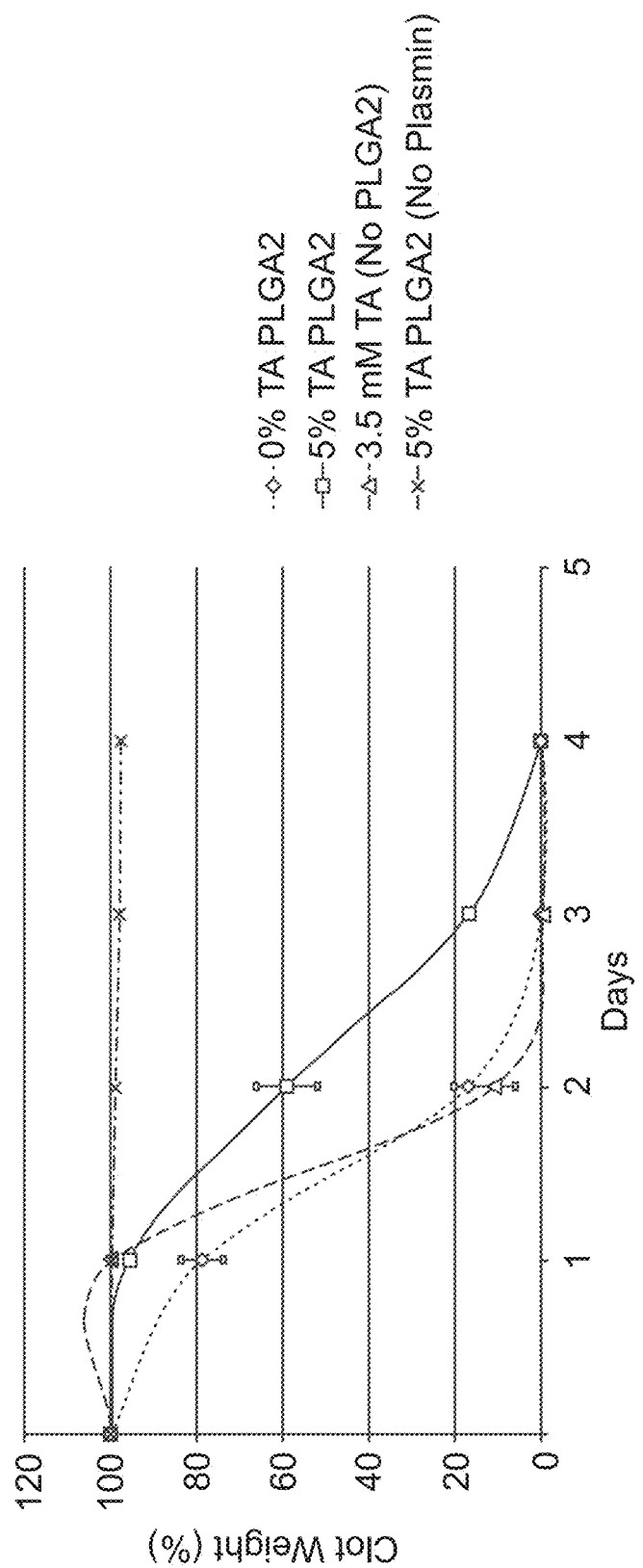
FIG. 19 illustrates a graph showing fibrin clot weight percent in a Plasmin medium as a function of time in days for loading level of 5.0 percent TA in PLGA-2 containing clot as compared to a control of loading level of 0 percent TA containing clot; also shown are results of 5.0 percent TA/PLGA-2 in a no Plasmin medium, as well as TA without any PLGA-2. These results of TA with PLGA-2 may be compared with those in FIG. 7 with TA in PLGA.

FIG. 19 illustrates a graph showing fibrin clot weight percent in a Plasmin medium as a function of time in days for loading level of 5.0 percent TA in PLGA-2 containing clot as compared to a control of loading level of 0 percent TA containing clot; also shown are results of 5.0 percent TA/PLGA-2 in a no Plasmin medium, as well as TA without any PLGA-2. These results of TA with PLGA-2 may be compared with those in FIG. 7 with TA in PLGA.

In further detail, a release study method for TA using high-performance liquid chromatography and mass spectrometry detection ("HPLC/MS") with direct auto-sampler injection has been developed. Mass Spectral detector with electrospray ionization ("ESI") (MS positive ion mode ionization) shows that TA from 5 percent TA/PLGA loaded microspheres is released slowly over a period of 144 hours (or 6 days) up to about seventy-two percent. TA from TA/PLGA microspheres releases at a slower rate after the initial seventy hours approximately.

Also, a gravimetric in vitro method has been developed for a degradation study of a fibrin sealant in a plasmin medium at pH 7.4 and 37° C., where the medium has been freshly exchanged every twenty-four hours. Further investigation into the described degradation of fibrin sealant was undertaken for up to four consecutive days. Both five weight percent and thirty percent TA loaded microspheres at a constant concentration of TA has shown significantly reduced percentage degradation of fibrin clot as compared to the control at the same period. Thus, the proof of principle of improving longevity of the fibrin sealant via sustained release has been demonstrated.

The current invention sets forth a system and in vivo method of delivery of a protease inhibitor, such as, but not limited to, aprotinin and/or tranexamic acid ("TA") to a wound site. In detail, a protease inhibitor composition including the calcium salt of TA (hereinafter "Ca-TA"), a new entity, has been prepared. Ca-TA demonstrates unexpected behavior of sustaining protease inhibiting activity and thus aids overall fibrin sealant longevity. Accordingly, a Ca-TA compound incorporated in a PLGA absorbable polymer microsphere has been prepared to impart longevity to fibrin sealant in an proteolytic environment via sustained release behavior.

Moreover, a method for delivering a preparation of aprotinin incorporated in PLGA absorbable polymer microsphere to a fibrinogen solution has been developed to show a delayed fibrin-based blood clot degradation time.

In detail, two systems of delivering aprotinin loaded microspheres were developed, for example, one at 3.3 percent aprotinin loading and another at 5.0 percent aprotinin loading. Results obtained show a similar fibrin-based blood clot degradation profile as that of TA as discussed above, particularly at the 5.0 percent TA loading level. Further, a slower release of the embedded aprotinin was noticed at the 3.3 percent loading level as opposed to 5.0 percent, thus indicating a possible trend that lower aprotinin loading levels are associated with slower aprotinin release profiles.

EXAMPLES

The following examples illustrate the invention, but are not intended to limit the claims in any manner whatsoever.

Example 1

A preparation of TA in PLGA at 5 percent loading for sustained release was prepared having the ingredients listed in the Table 1 below:

TABLE 1

(1) TA with an average particle diameter of 3.3 micron where the particle
diameter does not exceed 13 micron TABLE 1-continued (2) PLGA with an intrinsic viscosity of 0.44 dl/gm in hexafluoroisopropanol (hereinafter "HFIP") at 25° C. and a glass transition temperature of 37° C. to 44° C. as established by differential scanning calorimetry
(3) Dichloromethane ("DCM") where a suspension of TA in DCM may be dried and run by thermogravimetric analysis ("TGA") and x-ray powder diffraction ("XRPD") to demonstrate that DCM has not altered the structure of TA
(4) Polydimethylsiloxane ("PDMS") with a viscosity of 350 cSt
(5) Cyclomethicone, for example D-5 cyclic siloxane, decamethylcyclopentasiloxane, also known as Mirasil ® CM-5 from Bluestar Silicones The formulation of Example 1 was prepared as follows:
1. Make a 2.5 wt. percent solution of PLGA in DCM by dissolving 0.53 g of PLGA in 20.5 g DCM by magnetic stirring in a beaker.
2. Add 0.028 g of micronized TA to the 2.5 wt. percent solution of PLGA in DCM. Homogenize to breakdown any resultant agglomerate. The loading of TA in PLGA is 5.0 wt. percent.
3. Over the next several minutes, slowly add 37.5 g of linear siloxane, DL-350 cSt. The ratio of DCM to DC-350 is approximately 1.0:1.8. Mix the resultant milky liquid for a few more minutes.
4. Place 750 g of cyclomethicone in a jar fitted with an overhead propeller stirrer. Quickly transfer the above milky liquid to the cyclomethicone while stirring to allow for PLGA microsphere hardening. The ratio of the milky liquid (58 g) to cyclomethicone (750 g) is about 1:13.
5. Stir the mixture for 2.0 hours at approximately 500 revolutions per minutes ("RPM").
6. Filter with at least a 10 micron filter. Preferably, use a 0.2 micron Millipore filter.
7. Dry to for two days under vacuum at ambient temperature (for example, 21° C.). Measure the weight of the powder produced to calculate a percentage yield.

In the experiments conducted, a substantial amount of PLGA microspheres adhered to an interior wall of the surrounding container to produce an estimated yield of >60 percent. Further, continuous drying of the PLGA microspheres at 35° C. in a lyophilizer over one or two weeks has shown that residual DCM may be reduced to below 5 µg/mg PLGA microsphere (a possible upper acceptance limit in certain applications).

Example 2

A preparation of TA in PLGA at 30 percent loading for sustained release was prepared according to method set forth in Example 1 above with the following alterations.
The formulation of Example 2 was prepared as follows:
1. Use a proportionately higher amount of TA, e.g. 0.166 g TA, to prepare a loading of 30 wt. percent TA in PLGA.
2. Also, penta-cyclomethicone, the cyclic pentamer, may be replaced with a cyclic tetramer, D-4, for example from Bluestar Silicones.

Example 3

The formulation of Example 2 (i.e. 30 wt. percent TA in TA/PLGA microspheres) was characterized as follows:
1. Use an optical or a Scanning Electron Microscope ("SEM") to characterize as shown in FIG. 1A or 1B. The average diameter of the TA/PLGA microsphere was observed to be approximate 40 micron.
2. Use Confocal-Raman Spectroscopy to characterize the 30 wt. percent TA in TA/PLGA microspheres as shown in FIGS. 2A, 2B and 2C. As shown in FIGS. 2A, 2B and 2C, it was observed that TA was distributed towards the center of the PLGA microsphere, which was desirable for sustained release.

Example 4

A characterization of the release profile of TA in PLGA at 5 percent loading was conducted by an experiment as described herein.

TA entrained PLGA microspheres were placed in a buffered solution in a release chamber. The release of TA into the buffer was monitored over time and quantitated using quantitative LCMS (liquid chromatography with mass spec) analysis with an internal mass spec (MS) standard.

TA concentrations were quantitated in concentrations of 5 ppm (0.005 mg/mL, 0.032 mM) and higher using a high performance liquid chromatography mass spectral detector ("HPLC-MS"). A small liquid sample (5 µL) was injected using an auto-sampler through a blank column (C18 guard cartridge) into a mass spectral detector using electrospray ionization (ESI) and monitoring the molecular ion using either Single Ion Monitoring (SIM), or Extracting the Ion Content of interest (EIC) (M+1, positive ion mode) of TA compared to an internal standard at a constant concentration in the buffered solution, such as 4-aminobutyric acid.

Either EIC or SIM may be used to quantitate a signal belonging to a specific compound, in the case of tranexamic acid, m/z 158, (M+1) and an internal standard (4-aminobutyric acid) of m/z 104 (M+1). With a constant concentration of 4-aminobutyric acid in the buffer, the signals of repeated samples could be normalized to the signal of the internal standard, allowing a simple method for monitoring and determining tranexamic acid concentration changes over time. The specific signals were monitored throughout the run, and each signal was integrated over the course of the run. No need existed to physically separate the compounds via a chromatography column since the compounds had unique mass signals which could be independently monitored.

Either SIM or EIC was used to monitor the two masses of interest (internal standard, m/z 104, and TA m/z 158). EIC was used to scan from 100 to 200 mass units. The area defined by each EIC peak was later integrated.

To obtain a sensitivity and linear quantitation that might be usable under the experimental conditions, several HPLC mobile phase buffers were investigated. The most consistent system was a mobile phase consisting of 1 wt. percent methanol in water with 0.1 wt. percent formic acid. The quantitative samples were measured gravimetrically using a NIST traceable micro balance (±0.2 µg). Analysis was done directly on the removed sample with an injection of 5 µL onto an Agilent 1100 HPLC system attached to an HP 1100 LC/MSD with electrospray ionization. The flow rate was 0.3 mL/min, and each individual ion was monitored or extracted and integrated. Mass measurements were made with a Mettler AT20 micro balance calibrated with NIST traceable weights.

Samples were collected at a pre-selected time and sealed in an auto-sampler vial with a small volume insert. Samples were measured by HPLC/MS along with a set of TA standards in buffer in two batches.

General experimental conditions included weighing TA entrained microspheres (20 mg, in duplicate) onto 20 micron screens and assembling related release chambers. A separate set of placebo microspheres with no TA entrained (20 mg) were assembled. Each release assembly was placed into a conical centrifuge tube. Buffer (100 mM phosphate buffer, pH 7.40, 3 mL) was then added containing the mass spectral internal reference standard 4-aminobutyric acid (0.1 mg/mL) and rotated at approximately 100 rpm at 37° C. Samples (25 uL) were removed at times 0, 13, 24, 48, 72, 96, 120, and 144 hours and analyzed directly by ESI mass spectral analysis as described above.

The results of TA release are shown graphically in FIGS. 3A and 3B. FIG. 3A is expressed as the mM concentration of TA. FIG. 3B is expressed as percent release, assuming a 5 percent loading of TA in the microspheres.

TA has been reliably quantitated between 0.01 and 2 mM concentrations when measured against an internal standard. Correlation coefficients ranged from 0.9969 to 0.9856 for linearity between 0.01 and 2 mM concentration. For the purposes of the experiment, a standard curve between 0.01 and 1 mM was used as a calibration curve for each set of samples analyzed. Samples were taken from:
1. A blank release chamber with buffer as a negative control
2. A release chamber charged with placebo microsphere alone as a negative control
3. A release chamber charged with 5 percent TA loaded TA/PLGA microspheres
4. A second, identical release chamber as 3 above Each chamber except for 1 contained microspheres (20 mg) in a release chamber and 3 mL of buffer (100 mM phosphate, with 0.1 mg/mL 4-aminobutyric acid as an internal MS standard). Sample 1 contained an empty release chamber and 3 mL of buffer. In order to simplify the experiment the same buffer was kept in the solution and small aliquots were removed at the appropriate time intervals.

Samples were collected at the appropriate times (25 µL), then sealed in an auto-sampler vial, and two batches were analyzed with a series of TA calibration standards. The concentrations were determined from the calibration table using the areas of the M+1 ion signal for TA, and the m/z 104 signal from the internal standard. The negative standards analyzed uniformly negative for TA, and at the time "0" the samples were below the limit of detection for TA. Only the internal standard ion signal was observed.

The calibration curves displayed excellent linearity between 0.01 and 1 mM, however, the TA has been measured over the course of the experiment to almost 2 mM concentrations. Separate experiments (unpublished data) demonstrated linearity between 0.01 and 2 mM concentrations in buffer.

TA was released steadily for at least 144 hours when the experiment was stopped as shown in FIGS. 3A and 3B. The experiment demonstrates that TA could be entrained in PLGA microspheres at 5 percent loading of TA and slowly released into the surrounding media without showing any sudden or "burst" release. Release appeared to slow down after the initial 3 days (or about 72 hours).

Example 5

A hydrolytic degradation profile of placebo PLGA microsphere in de-ionized water was characterized at 37° C., as shown in FIG. 4. The profile was monitored by titration of acid produced by ester hydrolysis where a base was added to maintain a constant pH of 7.4. Observance of the profile suggested that approximately 80 percent of the PLGA microspheres degraded in about 34 days. As observed, the degradation profile was considered suitable because 34 days was a longer duration than the typical duration of fibrin sealant degradation. Alternatively, other suitable absorbable polymers might also be selected to form the microsphere.

Example 6

A gravimetric method of characterizing enzymatic degradation of the fibrin clot or sealant in the presence of TA/PLGA microspheres was conducted as described herein.

Experiments for the following three objectives were carried out to test the longevity of fibrin clot with sustained release of TA from 5 percent and 30 percent loaded TA in TA/PLGA microsphere samples in a plasmin medium.

Materials included, Table 2:

TABLE 2

(1) Bovine fibrinogen (Sigma F8630)
(2) Phosphate buffered saline (pH 7.4)
(3) Water bath (37° C.)
(4) 5 percent and 30 percent TA loaded TA/PLGA microspheres
(5) Incubator (37° C.)
(6) Thrombin (Sigma: T6634)
(7) Well plates (96)
(8) Plasmin (Sigma P1867)
(9) Calcium Chloride (Sigma C3306)
(10) Microfuge tubes, micro tips, micropipettes
(11) Weighing balance The first objective was to test the longevity of fibrin clot with varying concentrations of TA in plasmin medium. A preparation of fibrinogen solution containing TA was prepared as described herein:
1. Prepared a 10 percent solution of fibrinogen by dissolving 200 mg of bovine fibrinogen (Sigma F8630) in 2 ml of PBS. The solution was incubated at 37° C. with occasional swirling for 1 hour or until the fibrinogen was entirely dissolved.
2. Molecular weight of TA is 157 g. A 100 millimolar ("mM") stock solution of TA was prepared by dissolving 15.7 mg in 1 ml De-ionized water.

The following amounts from the stock solution were added to 10 percent fibrinogen solution as shown below in Table 3:

TABLE 3

| TA Concentration | 100 mM TA/300 µl |
| --- | --- |
| 0.00 mM | — |
| 0.10 mM | 0.3 µl |
| 0.25 mM | 0.75 µl |
| 0.50 mM | 1.5 µl |
| 1.00 mM | 3 µl |

The 300 microliter fibrinogen solution was divided later into 3 aliquotes of 100 microliters later.

Next, the fibrin clots in the ninety-six well plate were prepared as follows:
1. 0.5 mg Thrombin (600 units/mg) was dissolved in 200 µl of 375 mM $CaCl_2$ solution in phosphate buffered saline ("PBS") (1500 U/ml).
2. Seven microliters (10.5 U) were added to each well of the 96 well plate prior to the addition of 100 µl aliquots of 10 percent fibrinogen, and TA were mixed by pipetting and incubating at 37° C. temperature for 1 hour. Final concentration of CaCl₂ was observed at 25 mM.
3. The plate was stored at 4° C. overnight after the clot was formed.

It was observed during the experiment that the fibrin clot formation was instant or occurred in less than 15 seconds.

Next, plasmin was added to the fibrin clot to begin the enzymatic degradation of the fibrin clot by the plasmin as described herein:
1. A 300× plasmin solution was prepared by dissolving 500 μg in 500 μl PBS.
2. A 3× plasmin solution was prepared by diluting the 300× plasmin solution 100 times in PBS. 100 μl of the fibrinogen solution was already present in each well. Next, 200 μl of 3× plasmin solution was added to each well of the 96 well plate to dilute the 3× plasmin solution 1.5 times to prepare a final 2× concentration of plasmin solution at 6.6 μg/ml in the fibrinogen solution.
3. Incubation was set at 37° C. for 48 hours.

Data was collected as follows:
1. The 96 well plate was centrifuged at 1000 rpm for 5 minutes at room temperature. The supernatant solution containing plasmin was aspirated out with a micropipette to leave a clot at the bottom of the well. The supernatant was stored for later analysis.
2. The clots were removed from the well with a pair of forceps and weighed. The percentage degradation was calculated by 100−(Average wt of the plasmin treated clot/actual weight of the clot×100). The actual average weight of the clot before plasmin degradation has been 108 mg.
3. The clots were placed on a glass slide and photographed.

The weights of the clots have been recorded as follows, where A, B and C represent three independent sets, Table 4:

TABLE 4

| TA Concentration | A (mg) | B (mg) | C (mg) | Average Weight (mg) | Std. Dev. | Percentage Degradation |
|---|---|---|---|---|---|---|
| 0.00 mM | 14 | 16 | 14 | 14.7 | 1.2 | 86.3 |
| 0.10 mM | 96 | 99 | 91 | 95.3 | 4.0 | 11.8 |
| 0.25 mM | 108 | 104 | 82 | 98.0 | 14.0 | 9.3 |
| 0.50 mM | 102 | 106 | 108 | 105.3 | 3.1 | 2.5 |
| 1.00 mM | 100 | 108 | 106 | 104.7 | 4.2 | 3.0 |
| 0.00 mM + No Plasmin | 108 | 109 | 107 | 108 | 1.0 | 0 |

The above data supports that a 0.1 mM concentration of TA provides effective resistance against fibrin clot degradation by plasmin. Also, no significant increase in activity was observed by using more than 0.1 mM TA. Thus, the 0.1 mM (which is same as 157 ppm) concentration was sufficient for maximum activity. Further, it may be possible that even less than 0.1 mM concentration was sufficient to provide resistance to plasmin degradation. The above observations are shown in FIG. 5 in graphical form.

The second objective is to test the longevity of fibrin clot containing 30 weight percent TA loaded in TA/PLGA microspheres in a plasmin medium.

Fibrinogen solution containing 30 percent TA in TA/PLGA was prepared as described herein:
1. Prepared a 10 percent solution of fibrinogen by dissolving 100 mg of bovine fibrinogen (Sigma F8630) in 1 ml of PBS. The solution was incubated at 37° C. with occasional swirling for 1 hour or till fibrinogen is completely dissolved. 10 weight percent of Fibrinogen is 294.12 micromolar.
2. Molecular weight of TA is 157 g. A 10 millimolar (1.57 mg/ml) and 20 millimolar (3.14 mg/ml) suspension of 30 percent TA loaded TA/PLGA was prepared by dispersing 1.7 mg and 3.4 mg of 30 percent TA/PLGA in 300 microliter of 10 percent fibrinogen solution respectively, Table 5.

TABLE 5

| TA Concentration | 30 wt. percent TA-PLGA/ 300 μl | Final TA/ml |
|---|---|---|
| 0 mM | — | — |
| 10 mM | 1.57 mg | 1.57 mg |
| 20 mM | 3.14 mg | 3.14 mg |

The 300 microliter fibrinogen solution was divided later into 3 aliquots of 100 microliters later in 96 well plates and incubated at room temperature for one hour.

The fibrin clots in the ninety-six well plate were prepared as follows:
1. 0.5 mg of Thrombin (600 units/mg) was dissolved in 200 microliter of 375 mM CaCl₂ solution in PBS (1500 U/ml).
2. Seven microliters (10.5 U) were added to each 100 microliter aliquots of 10 percent fibrinogen, and 30 percent TA/PLGA in the 96 well plate, mixed by pipetting and incubated at 37° C. temperature for 1 hour. Final concentration of CaCl₂ was measured at 25 mM.
3. The plate has been stored at 4° C. overnight after the clot was formed.

It was observed during the experiment that the fibrin clot formation was instantaneous or in less than 15 seconds.

Next, plasmin was added to the fibrin clot to begin the enzymatic degradation of the fibrin clot by plasmin as described herein:
1. A 300× plasmin solution was prepared by dissolving 500 micrograms in 500 microliter PBS.
2. A 3× plasmin solution was prepared by diluting the 300× plasmin solution 100 times in PBS. 100 μl of the fibrinogen solution was already present in each well. Next, 200 μl of 3x plasmin solution was added to each well of the 96 well plate to dilute the 3× plasmin solution 1.5 times to prepare a final 2× concentration of plasmin solution at 6.6 μg/ml in the fibrinogen solution.
3. Incubation was set at 37° C. for 48 hours.

Data was collected as follows:
1. The 96 well plate was centrifuged at 1000 rpm for 5 minutes at room temperature. The supernatant plasmin solution was aspirated out with micropipette leaving the clot at the bottom of the well. The supernatant was stored for later analysis.
2. The clots were picked up from the well with a pair of forceps and weighed. The percent degradation was calculated by 100 minus(Average weight of the plasmin treated clot/actual weight of the clot×100). The actual weight of the clot before plasmin degradation was 108 mg.
3. The clots were placed on a glass slide and photographed.
4. The weights of the clots were recorded as follows, where A, B and C represent three independent sets, Table 6:

TABLE 6

| TA Concentration | A (mg) | B (mg) | C (mg) | Average Weight (mg) | Std. Dev. | percentage Degradation |
|---|---|---|---|---|---|---|
| 0 mM | 10 | 15 | 12 | 12.3 | 2.5 | 87 |
| 10 mM | 86 | 91 | 88 | 88.3 | 2.5 | 18 |
| 20 mM | 101 | 95 | 90 | 95.3 | 5.5 | 12 |

The above data supports that a 10 mM concentration of 30 percent TA/PLGA provides effective resistance against fibrin clot degradation by plasmin. Also, no significant increase in activity was observed by using 20 mM 30 percent TA/PLGA. Accordingly, the 10 mM concentration was sufficient for maximum activity. Even less than 10 mM concentration was sufficient to provide resistance to plasmin degradation. The above observations are shown in FIG. 6 in graphical form.

The third objective is to test the longevity of fibrin clot containing 5 weight percent TA and 30 weight percent TA loaded in TA/PLGA microspheres in a plasmin medium.

A preparation of fibrinogen solution was prepared as described herein:
1. Prepared a 10 percent solution of fibrinogen by dissolving 1.4 gms of bovine fibrinogen (Sigma F8630) in 14 ml of PBS. The solution was incubated at 37° C. with occasional swirling for 1 hour or till fibrinogen is completely dissolved.
2. Molecular weight of TA is 157 grams. Three and half millimolar (0.55 mg TA/ml) suspension of 5 percent and 30 percent TA/PLGA were prepared by dispersing 50 mg of 5 percent loaded TA/PLGA and 8.3 mg of 30 percent loaded TA/PLGA in 4.5 ml of 10 percent fibrinogen solution, respectively, Table 7. A 10 percent Fibrinogen solution without TA was used as the negative control.

TABLE 7

| 5 percent TA-PLGA/ml | 30 percent TA-PLGA/ml | Final TA/ml |
|---|---|---|
| 11.11 mg | 1.85 mg | 3.5 mM |

Next, the fibrin clots in the ninety-six well plate were prepared as follows:
1. Ninety-six well plates were labeled as shown in Tables 8 and 9.
2. Two and a half mg of Thrombin (600 units/mg) were dissolved in 1 ml of 375 mM $CaCl_2$ solution in PBS (1500 U/ml). Seven microliters (10.5 U) were added to each well of the labeled 96 well plates.
3. The fibrinogen solutions (with no TA/PLGA that is 0 percent, 5 percent loaded TA/PLGA and 30 percent loaded TA/PLGA) were mixed well and 100 microliter aliquots of 10 percent fibrinogen with or without TA/PLGA were added to the wells containing thrombin solution. The stock solutions were mixed in between to ensure that the microspheres did not settle to the bottom.
4. The plates were incubated at 37° C. temperature for one hour. Final concentration of $CaCl_2$ was 25 mM. The plate was stored at 4° C. overnight after the clot was formed. It was noted that the fibrin clot formation was either instantaneous or it formed in less than fifteen seconds.

Next, plasmin was added to the fibrin clots to begin the enzymatic degradation of the fibrin clots by plasmin as described herein:

1. A 300× plasmin solution was prepared by dissolving 500 micrograms in 500 microliter PBS. A 2× stock was prepared by diluting 150 times in PBS and adding 100 microliters to each well of the 96 well plate. The final 1× concentration was 3.3 micrograms/ml in the solution. A no-plasmin PBS only control was used for each condition.
2. Incubation was at 37° C. At every 24 hours, the 96 well plate was centrifuged at 1,000 rpm for five minutes at room temperature. The supernatant plasmin solutions were aspirated out from each well with micropipette leaving the clots at the bottom of the well.
3. A set of fibrin clots for each condition each day were taken out for measuring their degradation by plasmin by weighing. Fresh 100 microliter of plasmin solution was added to the rest of the clots. Fibrin clots were removed for measuring their weights each day until the clots were completely degraded in the wells.

Data was collected as follows:
1. The clots were picked up from the well with a pair of forceps and weighed. The percent degradation was calculated by 100−(Average wt of the plasmin treated clot/actual weight of the clot×100).
2. The clots were placed on a glass slide and photographed.

The weights of the fibrin clots were recorded at an interval of one day (or 24 hours) as follows, where A, B and C represent three independent sets, Table 8:

TABLE 8

| Day | TA/PLGA | A (mg) | B (mg) | C (mg) | Average Weight (mg) | Std Dev | percent degradation |
|---|---|---|---|---|---|---|---|
| 0 | 0 percent | 108 | 109 | 107 | 108.0 | 1.0 | 0 |
| 1 | 0 percent | 85 | 82 | 84 | 83.7 | 1.5 | 23 |
| 2 | 0 percent | 9 | 6 | 8 | 7.7 | 1.5 | 93 |
| 3 | 0 percent | 0 | 0 | 0 | 0.0 | 0.0 | 100 |
| 4 | 0 percent | 0 | 0 | 0 | 0.0 | 0.0 | 100 |
| 0 | 5 percent | 112 | 112 | 113 | 112.3 | 0.6 | 0 |
| 1 | 5 percent | 98 | 88 | 90 | 92.0 | 5.3 | 18 |
| 2 | 5 percent | 83 | 74 | 70 | 75.7 | 6.7 | 33 |
| 3 | 5 percent | 21 | 15 | 18 | 18.0 | 3.0 | 84 |
| 4 | 5 percent | 0 | 0 | 0 | 0.0 | 0.0 | 100 |
| 0 | 30 percent | 110 | 109 | 110 | 109.7 | 0.6 | 0 |
| 1 | 30 percent | 96 | 99 | 93 | 96.0 | 3.0 | 12 |
| 2 | 30 percent | 73 | 86 | 75 | 78.0 | 7.0 | 29 |
| 3 | 30 percent | 22 | 16 | 20 | 19.3 | 3.1 | 82 |
| 4 | 30 percent | 0 | 0 | 0 | 0.0 | 0.0 | 100 |

The above observations are shown in FIG. 7 in graphical form.

The weights of the fibrin clots in a medium containing no plasmin were recorded on Day-4, as shown in Table 9:

TABLE 9

| Day | TA/PLGA | A (mg) | B (mg) | C (mg) | Average Weight (mg) | Std Dev | percent degradation |
|---|---|---|---|---|---|---|---|
| 4 | 0 percent | 108 | 106 | 105 | 106.3 | 1.5 | 2 |
| 4 | 5 percent | 110 | 109 | 110 | 109.7 | 0.6 | 2 |
| 4 | 30 percent | 109 | 108 | 107 | 108.0 | 1.0 | 2 |

The above data support that fibrin clots without TA show 100 percent degradation between Day-2 and Day-3 as shown in FIGS. 7 and 8. Fibrin clots with TA/PLGA show 100 percent degradation on Day-4. Fibrin clots with or without TA/PLGA were not degraded in a "no plasmin containing medium" as observed in Table 8. Sustained release of TA delayed fibrin clot degradation in a plasmin containing medium. On Day-2, it was observed that TA/PLGA containing fibrin clots showed significant resistance to degradation by plasmin as compared to a control that contained no TA. Significant differences between fibrin clots with TA/PLGA and fibrin clots without TA/PLGA were observed on Day-3 also as observed in FIGS. 7 and 8. No significant difference was observed between 5 percent and 30 percent loaded TA in TA/PLGA in the fibrin clots in providing resistance to plasmin degradation. The results are summarized in Table 10. It is observed that the controls of 0 percent, 5 percent and 30 percent TA/PLGA without any plasmin displayed only 2 percent degradation or less up to Day-4, when the experiment was stopped, Table 10.

TABLE 10

| TA/PLGA Microsphere In Fibrin Clot | | Fibrin Sealant percent Degradation as a Function of Time in Days | | | | | |
|---|---|---|---|---|---|---|---|
| | | Day-0 | Day-1 | Day-2 | Day-3 | Day-4 | Day-4 (without Plasmin) |
| Control 0 percent TA/PLGA | 0 mM | 0 +/− 1.0 percent | 23 +/− 1.5 percent | 93 +/− 1.5 percent | 100 +/− 0 percent | 100 +/− 0 percent | 2 +/− 1.5 percent |
| 5 percent Loaded TA/PLGA (11.11 mg/ml) | Calculated Final TA = 3.5 mM | 0 +/− 0.6 percent | 18 +/− 5.3 percent | 33 +/− 6.7 percent | 84 +/− 3.0 percent | 100 +/− 0 percent | 2 +/− 0.6 percent |
| 30 percent Loaded TA/PLGA (1.85 mg/ml) | Calculated Final TA = 3.5 mM | 0 +/− 0.6 percent | 12 +/− 3.0 percent | 29 +/− 7.0 percent | 82 +/− 3.1 percent | 100 +/− 0 percent | 2 +/− 1.0 percent |

Example 7

A Calcium Tranexamate (or Calcium bis-Tranexamate, or Ca-TA) preparation and characterization was conducted as described herein. Ca-TA was prepared from a methanolic solution of Calcium Nitrate and a solution of Potassium Tranexamate which was itself prepared from Tranexamic Acid and solid Potassium Hydroxide dissolved in anhydrous methanol. A white powder slowly appeared and precipitated upon stirring overnight at room temperature, which was collected and dried.

The NMR spectra and data are shown in FIGS. 9A, 9B, 9C, 9D and 9E. Proton NMR analysis of the isolated and dried white powder shows no starting Tranexamic Acid, or Potassium Tranexamate, but a new species that has the same proton NMR splitting pattern as Tranexamic Acid, but with different ppm values. The 5-proton of Calcium Tranexamate is diagnostic as a distinctive signal at 1.46 ppm (ttt, J=11.4, 7.6, 3.8) appearing as a complex multiplet significantly downfield from its counterpart in Tranexamic Acid which is a zwitterion. The charged amino group affects the protons of the 6, 4 and 4 to move their resonance values downfield relative to the free base that is found in the Calcium Tranexamate.

Example 8

A Ca-TA preparation in PLGA microspheres at 5 weight percent loading for sustained released was conducted as described herein.

Materials required for the preparation of Ca-TA are the same as set forth in Example 1, excepting that Ca-TA has been prepared as described in Example 7 and substituted for TA.

The formulation of Example 8 was prepared as follows:

1. Place 0.028 gm Ca-TA in a conical flask. Use a magnetic stirrer in DCM to break down any agglomerates as done with TA.
2. Add 0.53 gm PLGA powder to the same conical flask. Add 20.5 gm DCM so that it makes a solution of PLGA in DCM of 2.5 percent. Start magnetic stirring in the conical flask by covering it for 0.5 hour. Ca-TA, DCM and PLGA make a visually solid-free, but turbid and/or translucent solution. Ca-TA was observed to be homogenized in the manner described.
3. The loading of Ca-TA in PLGA is 5 weight percent in above composition.
4. Add, over several minutes, 37.5 gm of the linear polydimethylsiloxane, DC-350 cSt, to the turbid solution. The ratio of DCM to DC-350 is about 1.0:1.8. Continue to mix the milky liquid for several more minutes
5. Place 850 g cyclomethicone (Tetramer D-4 from Bluestar) in a jar fitted with an overhead propeller stirrer. Transfer the above milky liquid containing polydimethylsiloxane with a dropper to the cyclomethicone while stirring. The ratio of milky liquid (58 g) to cyclomethicone (850 g) is about 1 to 14.
6. Continue with the above hardening step for 2 hours with stirring at about 500 rpm.
7. Filter with at least a 10 micron filter; or use 0.2 micron (use 0.22 micron vacuum filtration set up from Millipore; model—Stericup & Steritop vacuum-driven disposable filtration system & accessories.)
8. Dry for two days under vacuum at ambient temperature (e.g. 21° C.) Measure weight of powder and calculate a percentage yield. Observations of the experiment indicated that a significant amount of precipitate adhered to an interior wall of the plastic container in which the solution was placed. This gave an estimated yield of about 57 percent.
9. Determine particle size of Ca-TA/PLGA microspheres by TEM and TA release rate by HPLC-MS.

FIG. 10 illustrates SEM data on size distribution of Ca-TA/PLGA microsphere. An EDX(energy dispersive X-ray) analysis has shown the presence of Calcium in the microsphere.

Example 9

The longevity of fibrin clot in the presence of 5 percent Ca-TA loaded Ca-TA/PLGA microspheres and plasmin was evaluated as described herein. The molar equivalent weight of Calcium salt of Tranexamic Acid (Ca-TA) is 176 grams. A 10 milliEquivalent (1.76 mg/ml) and 20 milliEquivalent (3.53 mg/ml) suspension of 5 percent Ca-TA/PLGA were prepared by adding 10.6 mg and 21.1 mg of 5 percent Ca-TA/PLGA in 300 microliter of 10 percent fibrinogen solution prepared in PBS, respectively.

0.5 mg of Thrombin (600 units/mg) was dissolved in 200 microliter of 375 mM $CaCl_2$ solution in PBS (1500 U/ml). Seven microliters (10.5 U) were added to each well of the 96 well plate prior to the addition of 100 microliter aliquots of 10 percent fibrinogen and 5 percentCa-TA/PLGA, mixed by pipetting, and then incubated at 37° C. temperature for one hour. Final concentration of $CaCl_2$ was measured at 25 mM. The plate was stored at 4° C. overnight after the clot formed.

Plasmin solution was prepared such that the final 2× concentration of plasmin was 6.6 µg/ml in the solution. The clot, formed instantly, was incubated in the presence plasmin at 37° C. for 72 hours. Clots were then collected and weighed in the same manner as described earlier in Example 6.

Results showed that a 10 mE concentration of 5 percent CA-TA loaded Ca-TA/PLGA microspheres provided effective resistance against fibrin clot degradation by plasmin. No significant increase in activity was observed by using 20 mE 5 percent Ca-TA/PLGA, which suggested that the 10 mE concentration was sufficient for maximum activity. Thus, less than 10 mE concentration might be sufficient to provide resistance to plasmin degradation.

The next experiment was carried out using 5 percent Ca-TA loaded Ca-TA/PLGA microspheres in fibrin clot at 3.5 mE concentration of TA (or 0.62 mg Ca-TA per ml), which was prepared by placing 24.64 mg of 5 percent Ca-TA/PLGA microspheres in 2 ml of 10 percent fibrinogen solution. A 10 percent fibrinogen solution without Ca-TA was used as the negative control. The clot or sealant was exchanged with fresh plasmin solution of 3.3 micrograms/ml every 24 hours. The results are summarized in Table 11, which shows fibrin clot degradation in the presence of plasmin at 3.3 µg/ml in a PBS buffer of pH 7.4 at 37° C. The total concentration of Ca-TA was kept constant at 3.5 mE using 12.3 mg per ml of 5 percent Ca-TA loaded Ca-TA/PLGA microspheres. Also shown are control data without using any plasmin in Day-4, Table 11.

The results of Table 11 illustrated in FIG. 11 show that Ca-TA displays efficacy of sustained release from PLGA for improving longevity of fibrin clot sealant as compared to the control over a period of 4 days.

Example 10

The solubility aspects of Ca-TA was evaluated as described here in comparison with Calcium Nitrate, a highly water soluble salt:

Solution-I: Add Calcium Nitrate to 0.04 M to a 50 mM Tris buffer of pH 7.4 and observe turbidity. It was completely clear and transparent.

Solution-II: Add Calcium Tranexamate to 0.04 M to a 50 mM Tris buffer of pH 7.4 and observe turbidity. It was completely clear and transparent. (Molecular weight of Ca-TA was 352 g/mole which gave an equivalent weight of 176 g/Eq)

Solution-III: Add Calcium Nitrate to 0.004 M to a 50 mM phosphate buffer of pH 7.4 and observe turbidity. It showed turbidity.

Solution-IV: Add Calcium Tranexamate to 0.004 M to a 50 mM phosphate buffer of pH 7.4 and observe turbidity. It showed turbidity.

Based on the above results it was concluded that Ca-TA was water soluble like Calcium Nitrate. However, both would precipitate Calcium Phosphate in a PBS buffer.

Example 11

The next experiment was carried out in the same manner as illustrated in FIG. 5 for TA under Example 6, but TA was replaced with Ca-TA. The results with Ca-TA, in mE units, are shown in FIG. 12. A concentration of about 0.1 mE appear adequate to give a stable clot without any significant degradation.

The next experiment was carried out using 3 percent Ca-TA in fibrin clot. A 3 percent solution (169.5 mE Ca-TA and 30 mg/ml) of Ca-TA was prepared by dissolving 90 mg of Ca-TA in 3 ml of 10 percent fibrinogen solution. A 10 percent Fibrinogen solution without Ca-TA was used as the negative control. The clots were irrigated and exchanged with fresh plasmin solution of 3.3 micrograms/ml every 24 hours. The results are summarized in Table 12, which show fibrin sealant degradation in the presence of plasmin at 3.3 µg/ml in a PBS buffer of pH 7.4 at 37° C.

TABLE 11

| | | Fibrin Sealant percent Degradation as a Function of Time in Days | | | | | |
|---|---|---|---|---|---|---|---|
| Ca-TA/PLGA Microsphere In Fibrin Clot | | Day-0 | Day-1 | Day-2 | Day-3 | Day-4 | Day-4 but without Plasmin |
| Control 0 percent Ca-TA/ PLGA | 0 mM | 0 +/− 0 percent | 7 +/− 3.5 percent | 67 +/− 3.7 percent | 100 +/− 0 percent | 100 +/− 0 percent | 1 +/− 0 percent |
| 5 percent Loaded Ca-TA/PLGA (12.3 mg/ml) | Calculated Final Ca-TA = 3.5 mE | 0 +/− 0 percent | 7 +/− 2.8 percent | 19 +/− 2.5 percent | 74 +/− 6.6 percent | 100 +/− 0 percent | 1 +/− 0 percent |

TABLE 12

| Day | Ca-TA | A (mg) | B (mg) | C (mg) | Average Weight (mg) | Std Dev | percent degradation |
|---|---|---|---|---|---|---|---|
| 0 | 0 percent | 108 | 108 | 108 | 108.0 | 0.0 | 0 |
| 1 | 0 percent | 52 | 42 | 48 | 47.3 | 5.0 | 56 |
| 2 | 0 percent | 10 | 8 | 6 | 8.0 | 2.0 | 93 |
| 3 | 0 percent | 0 | 0 | 0 | 0.0 | 0.0 | 100 |
| 4 | 0 percent | 0 | 0 | 0 | 0.0 | 0.0 | 100 |
| 0 | 3 percent | 113 | 113 | 113 | 113.0 | 0.0 | 0 |
| 1 | 3 percent | 175 | 160 | 204 | 179.7 | 22.4 | N/A |
| 2 | 3 percent | 172 | 174 | 209 | 185.0 | 20.8 | N/A |
| 3 | 3 percent | 130 | 100 | 140 | 123.3 | 20.8 | N/A |
| 4 | 3 percent | 0 | 0 | 0 | 0.0 | 0.0 | 100 |

The results of Table 12 are illustrated in FIGS. 13 and 14, which show that Ca-TA displays efficacy of sustained release for improving longevity of fibrin clot or sealant as compared to the control over a period of 4 days without using any PLGA matrix. Fibrin clots with 3 percent Ca-TA gradually changed from a solid clot to a highly viscous semi-solid between Day-1 to Day-3, and finally turned liquid on Day-4. The clots turned highly absorbent over the incubation period and absorbed the plasmin solution resulting in increase in volume or weight on Day-1 and Day-2 by more than 50 percent of its original weight, as observed in FIGS. 13 and 14. Fibrin clots with 3 percent Ca-TA but without any plasmin also showed increase in volume or weight by Day-3 and Day-4 by more than 50 percent, as observed in FIGS. 13 and 14. However no significant volume or weight change was observed for fibrin clots without any Ca-TA in a medium containing no plasmin.

Example 12

A preparation of aprotinin in PLGA-2 at 3.3 percent and 5.0 percent loading for sustained release were prepared in the same manner as shown in Example 1. Aprotinin (bovine), recombinant version, in a powder form was procured from Sigma-Aldrich, A-6103-25 MG. It was expressed in Nicotiana, >=5 TIU/MG protein, >=98 percent (SDS_PAGE). It was a fine powder and was used without any further micronization.

Here the PLGA polymer was replaced by PLGA-2 polymer, which contained 0 percent glycine monomer. It was poly-L-Lactide procured from Lactel Absorbable Polymers, Durect Corp., Birmingham, Ala. PLGA-2 was expected to have slower degradation than PLGA, though both systems could generate aqueous channels early in microspheres for removal of hydrophilic protease inhibitor. For comparison of PLGA with PLGA-2, 5 percent TA/PLGA-2 was also prepared and evaluated.

Example 13

Next, an experiment to test the longevity of fibrin-based clot with the sustained release of aprotinin as incorporated into PLGA microspheres was conducted in a continuous plasmin medium.

The following materials, as listed in Table 13, were used:

TABLE 13

1) Bovine fibrinogen (Sigma F8630)
2) Phosphate buffered saline pH 7.4
3) 37° C. waterbath
4) TA-PLGA2 5 percent Loading TABLE 13-continued 5) Aprotinin-PLGA2 3.3 percent Loading
6) 37° C. incubator
7) Thrombin (Sigma: T6634)
8) 96 well plates
9) Plasmin (Sigma P1867)
10) Calcium Chloride (Sigma C3306)
11) Microfuge tubes, micro tips, micropipettes
12) Weighing balance A preparation of fibrinogen solution containing aprotinin and TA in PLGA-2 was made according to the following steps:
1. Prepared a 10 percent solution of fibrinogen by dissolving 0.6 grams of bovine fibrinogen (Sigma F8630) in 6 ml of PBS. The solution was incubated at 37° C. with occasional swirling for 1 hour or till fibrinogen is completely dissolved.
2. A 3.3 percent loading of aprotinin in PLGA-2 was prepared as follows:
   a. 0.033 mg Aprotinin/ mg Aprotinin-PLGA-2=214.5 KIU Aprotinin/mg Aprotinin-PLGA (1 mg=6500 KIU)
   b. 3000 KIU=13.98 mg Aprotinin- PLGA-2 required for each ml of 10 percent fibrinogen solution=4.19 mg/300 ml
   c. Using 5 fold higher for sustained release 20.95 mg (4.19 mg×5) required for each 300 ml of fibrinogen solution
   d. 174.58 mg of Aprotinin/PLGA-2 (69.83 mg/ml) was dissolved in 2.5 ml of 10 percent fibrinogen solution
3. Molecular weight of Tranexamic acid (TA) is 157 grams. Three and half millimolar (0.55 mg TA/ml or 11.11 mg TA-PLGA/ml) solution of 5 percent TA/PLGA2 was prepared by dissolving 28 mg of 5 percent TA/PLGA2 in 2.5 ml of 10 percent fibrinogen solution.
4. 10 percent Fibrinogen solutions without TA or Aprotinin or PLGA were used the negative control. In the PLGA-2 negative control 15000 KIU/ ml (3000×5 fold) Aprotinin were added (2.3 mg/ml or 0.7mg/300 ul).

Next, a preparation of fibrin-based clot was made as follows:
1. Ninety six well plates were labeled as shown in Table 1
2. 1.25 mg of Thrombin (600 units/mg) was dissolved in 0.5 ml of 375 mM CaCl2 solution in PBS (1500 U/ml). Seven microliters (10.5 U) were added to each well of the labeled 96 well plates.
3. The fibrinogen solutions (0 percent or 3.3 percent Aprotinin/PLGA-2 or 5 percent TA/PLGA-2) were mixed well and 100 microliter aliquots of 10 percent fibrinogen with or without Aprotinin/PLGA2 or TA/PLGA2 were added to the wells containing thrombin solution. The stock solutions were mixed in between to ensure that the particles do not settle to the bottom.
4. The plates were incubated at 37 C temperature for 1 hour. Final concentration of CaCl2 was 25 mM. The plate was stored at 4 C overnight after the clot was formed. NOTE: The fibrin clot formation was instant (less than 15 sec)

Continuing, the enzymatic degradation of the fibrin-based blood clot was further observed as follows:
1. A 300× plasmin solution was prepared by dissolving 500 micrograms in 500 microliter PBS. A 2×stock was prepared by diluting 150 times in PBS and 100 microliters added to each well of the 96 well plate. The final 1× concentration was 3.3 micrograms/ml in the solution. A no plasmin PBS only control was used for each condition.
2. Incubated at 37 C. At every 24 hours the 96 well plates were centrifuged at 1000 rpm for 5 minutes at room temperature. The supernatant plasmin solutions were aspirated out from each well with micropipette leaving the clots at the bottom of the well. A set of fibrin clots for each condition each day were taken out for measuring their degradation by plasmin by weighing. To the rest of the clots fresh 100 microliter of plasmin solution was added. Repeated till the clots completely disappeared.

Data was collected as follows:
1. The clots were picked up from the well with a pair of forceps and weighed. The percent degradation was calculated by 100−(Average wt of the plasmin treated clot/actual weight of the clot×100).
2. The clots were placed on a glass slide and photographed.

The weights of fibrin-based clots were observed as follows (where A, B and C represents three independent sets.)

TABLE 14

| Day | Aprotinin or TA in PLGA2 | A (mg) | B (mg) | C (mg) | Average Weight (mg) | Std Dev | percent degradation |
|---|---|---|---|---|---|---|---|
| 0 | 0 percent | 107.90 | 109.50 | 108.60 | 108.67 | 0.80 | 0.00 |
| 1 | 0 percent | 80.40 | 90.80 | 86.20 | 85.80 | 5.21 | 21.05 |
| 2 | 0 percent | 15.20 | 18.60 | 22.10 | 18.63 | 3.45 | 82.85 |
| 3 | 0 percent | 0.00 | 0.00 | 0.00 | 0.00 | 0.00 | 100.00 |
| 4 | 0 percent | 0.00 | 0.00 | 0.00 | 0.00 | 0.00 | 100.00 |

TABLE 15

| Day | Aprotinin/PLGA2 | A (mg) | B (mg) | C (mg) | Average Weight (mg) | Std Dev | percent degradation |
|---|---|---|---|---|---|---|---|
| 0 | 3.3 percent | 114.60 | 115.50 | 119.30 | 116.47 | 2.49 | 0.00 |
| 1 | 3.3 percent | 98.30 | 100.90 | 105.20 | 101.47 | 3.48 | 12.88 |
| 2 | 3.3 percent | 74.30 | 77.20 | 79.20 | 76.90 | 2.46 | 33.97 |
| 3 | 3.3 percent | 24.90 | 26.20 | 22.10 | 24.40 | 2.10 | 79.05 |
| 4 | 3.3 percent | 0.00 | 0.00 | 0.00 | 0.00 | 0.00 | 100.00 |

TABLE 16

| Day | Aprotinin (KIU) | A (mg) | B (mg) | C (mg) | Average Weight (mg) | Std Dev | percent degradation |
|---|---|---|---|---|---|---|---|
| 0 | 1500 | 109.30 | 108.50 | 109.60 | 109.13 | 0.57 | 0.00 |
| 1 | 1500 | 100.20 | 98.10 | 103.50 | 100.60 | 2.72 | 7.82 |
| 2 | 1500 | 14.60 | 13.80 | 16.70 | 15.03 | 1.50 | 86.22 |
| 3 | 1500 | 0.00 | 0.00 | 0.00 | 0.00 | 0.00 | 100.00 |
| 4 | 1500 | 0.00 | 0.00 | 0.00 | 0.00 | 0.00 | 100.00 |

TABLE 17

| Day | TA/PLGA2 | A (mg) | B (mg) | C (mg) | Average Weight (mg) | Std Dev | percent degradation |
|---|---|---|---|---|---|---|---|
| 0 | 5 percent | 110.40 | 110.30 | 110.60 | 110.43 | 0.15 | 0.00 |
| 1 | 5 percent | 106.80 | 106.00 | 105.30 | 106.03 | 0.75 | 3.98 |
| 2 | 5 percent | 58.60 | 74.30 | 63.80 | 65.57 | 8.00 | 40.63 |
| 3 | 5 percent | 16.90 | 20.20 | 18.70 | 18.60 | 1.65 | 83.16 |
| 4 | 5 percent | 0.00 | 0.00 | 0.00 | 0.00 | 0.00 | 100.00 |

Next, the weights of fibrin-based clots were observed in a medium without plasmin as follows in Table 18

TABLE 18

| Day | 0 percent Aprotinin Or TA in PLGA2 | 3.3 percent Aprotinin/PLGA2 | 5 percent TA/PLGA2 |
|---|---|---|---|
| 0 | 108.67 | 116.47 | 110.43 |
| 1 | 108.03 | 116.43 | 110.37 |
| 2 | 107.47 | 115.57 | 109.30 |
| 3 | 107.13 | 114.37 | 108.33 |
| 4 | 106.17 | 112.70 | 107.93 |
| percent Degradation on Day 4 | 2.30 | 3.24 | 2.26 |

Results with 5.0 percent Aprotinin/PLGA-2 are shown in Table 19 below

TABLE 19

| Day | Aprotinin/PLGA2 | A (mg) | B (mg) | C (mg) | Average Weight (mg) | Std Dev | percent degradation |
|---|---|---|---|---|---|---|---|
| 0 | 5 percent | 112.30 | 114.50 | 115.20 | 114.00 | 1.51 | 2.12 |
| 1 | 5 percent | 105.50 | 108.20 | 106.30 | 106.67 | 1.39 | 8.42 |
| 2 | 5 percent | 68.50 | 65.30 | 72.81 | 68.87 | 3.77 | 40.87 |
| 3 | 5 percent | 18.31 | 23.89 | 22.34 | 21.51 | 2.88 | 81.53 |
| 4 | 5 percent | 0.00 | 0.00 | 0.00 | 0.00 | 0.00 | 100.00 |

As shown by the above data tables:
1. Fibrin clots without aprotinin showed 100 percent degradation between day 2 and 3 (FIGS. 15 and 16).
2. Fibrin clots with 3.3 percent aprotinin/PLGA-2 showed 100 percent degradation on days between 3 and 4. No clots were present in the wells of the 96 well plate.
3. Fibrin clot with only 1500 KIU Aprotinin showed 100 percent degradation between day 2 and day 3.
4. Fibrin clots with or without aprotinin/PLGA-2 were not degraded in a no plasmin containing medium by end of day 4 (Table 14)
5. Sustained release of aprotinin delayed fibrin clot degradation in a plasmin containing medium. On day 2 and 3 Aprotinin/PLGA-2 containing fibrin clots showed significant resistance to plasmin compared with no Aprotinin containing clots or clots containing free aprotinin. (Tables 15 and 16, and FIGS. 15, 16 and 17)
6. A similar pattern was observed for 5.0 percent TA/PLGA-2 (Tables 17 and 18, and FIGS. 18 and 19)
7. A comparison of aprotinin/PLGA-2 of 3.3 percent loading versus 5.0 percent as shown in Tables 15 and 19, respectively, indicate that lower percent loading has a tendency to give a lower percent degradation, particularly in day 1 and 2, presumably due to slower release and slower diffusion away of protease inhibitor Although exemplary systems and methods are described in language specific to structural features and/or methodological acts, the subject matter defined in the appended claims is not necessarily limited to the specific features or acts described. Rather, the specific features and acts are disclosed as exemplary forms of implementing the claimed systems, methods and structures.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The invention claimed is:

1. A method comprising:
administering a composition that includes an inhibitor comprising calcium tranexamate, the inhibitor being encapsulated within a biodegradable microsphere, to a blood-containing site, wherein degradation of the biodegradable microsphere releases the inhibitor to the blood-containing site via a sustained release mechanism;
wherein the composition is configured to:
form a fibrin-based clot in the presence of the inhibitor during a time sufficient to degrade the biodegradable microsphere and cause the inhibitor to release from the biodegradable microsphere;
swell the fibrin-based clot to cause hemostasis; and
delay degradation of the fibrin-based clot at the blood-containing site;
wherein a weight and/or volume of the fibrin-based clot in the presence of the inhibitor is greater than a weight and/or volume of the fibrin-based clot not in the presence of the inhibitor.

2. The method of claim 1, wherein the composition includes a mixture of calcium tranexamate and tranexamic acid.

3. The method of claim 1, wherein the composition is provided to a patient experiencing Menorrhagia.

4. The method of claim 1, wherein the composition is provided orally.

5. The method of claim 1, wherein the composition further includes tranexamic acid encapsulated within the biodegradable microsphere.

6. The method of claim 1, wherein the biodegradable microsphere comprises a polymer of monomers selected from the group consisting of lactic acid, glycolic acid, caprolactone and combinations thereof.

7. The method of claim 1, wherein the blood-containing site comprises a wound site.

8. The method of claim 1, wherein the fibrin-based clot in the presence of the inhibitor comprises the inhibitor being in contact with the fibrin-based clot.

9. The method of claim 1, wherein the biodegradable microsphere releases the inhibitor to a proteolytic environment surrounding the blood-containing site.

10. The method of claim 1, wherein the method comprises an in vivo method.

* * * * *